(12) United States Patent
Barbas, III et al.

(10) Patent No.: US 7,087,409 B2
(45) Date of Patent: Aug. 8, 2006

(54) HUMANIZATION OF MURINE ANTIBODY

(75) Inventors: Carlos F. Barbas, III, San Diego, CA (US); Christoph Rader, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 301 days.

(21) Appl. No.: 10/078,757

(22) Filed: Feb. 19, 2002

(65) Prior Publication Data

US 2003/0166871 A1 Sep. 4, 2003

Related U.S. Application Data

(63) Continuation of application No. 08/986,016, filed on Dec. 5, 1997, now abandoned.

(51) Int. Cl.
| | |
|---|---|
| *C12P 21/04* | (2006.01) |
| *C12Q 1/70* | (2006.01) |
| *C12P 21/08* | (2006.01) |
| *C07K 16/00* | (2006.01) |
| *C07H 21/04* | (2006.01) |

(52) U.S. Cl. .................. 435/69.6; 435/5; 435/235.1; 435/320.1; 530/387.3; 530/388.1; 530/388.23; 536/23.53

(58) Field of Classification Search ............ 530/387.1, 530/389.88, 387.3, 388.1, 388.23; 435/69.6, 435/69.1, 235.1, 328, 320.1; 536/23.53
See application file for complete search history.

(56) References Cited

U.S. PATENT DOCUMENTS 5,565,332 A * 10/1996 Hoogenboom et al.
5,859,205 A * 1/1999 Adair et al.

OTHER PUBLICATIONS

Paul, Fundamental Immunology, Raven Press, NY, Chapter 8, p. 242, 1993.*
Brooks et al J. Clin. Invest. 96:1815-1822, 1995.*
Rader et al. Proc. Natl. Acad. Sci. USA, 95:8910-8915, Jul. 1998.*

* cited by examiner

*Primary Examiner*—Sheela Huff
*Assistant Examiner*—David J. Blanchard
(74) *Attorney, Agent, or Firm*—Olson & Hierl, Ltd.

(57) ABSTRACT

A humanized murine antibody is provided. The amino acid sequences of a light chain complementarity determining region from a mouse antibody are grafted onto a human light chain, and a heavy chain complementarity determining region from a mouse antibody are grafted onto a human antibody heavy chain to produce libraries from which a humanized murine antibody having the desired specificity is selected.

12 Claims, 14 Drawing Sheets

V$_\lambda$

Leu Glu Ser Gly Gly Gly Leu Val Lys Pro Gly Gly Ser Leu Lys Leu Ser Cys Ala Ala Ser
                    5                   10                  15                  20
Gly Phe Ala Phe Ser Ser Tyr Asp Met Ser Trp Val Arg Gln Ile Pro Glu Lys Arg Leu Glu Trp
                    25                  30                  35                  40
Val Ala Lys Val Ser Ser Gly Gly Ser Thr Tyr Tyr Leu Asp Thr Val Gln Gly Arg Phe Thr
45                  50                  55                  60                  65
Ile Ser Arg Asp Asn Ala Lys Asn Thr Leu Tyr Leu Gln Met Ser Ser Leu Asn Ser Glu Asp Thr
                    70                  75                  80                  85
Ala Met Tyr Tyr Cys Ala Arg His Asn Tyr Gly Ser Phe Ala Tyr Trp Gly Gln Gly Thr Leu Val
                    90                  95                  100                 105                 110
Thr Val Ser Ala Ala Lys Thr Thr Pro Pro Ser Val Tyr Pro Leu Ala Pro Gly Ser Ala
                    115                 120                 125                 130

FIGURE 2a

V$_\kappa$

Glu Leu Val Met Thr Gln Thr Pro Ala Thr Leu Ser Val Thr Pro Gly Asp Ser Val Ser Leu Ser
                    5                   10                  15                  20
Cys Arg Ala Ser Gln Ser Ile Ser Asn His Leu His Trp Tyr Gln Gln Lys Ser His Glu Ser Pro
                    25                  30                  35                  40
Arg Leu Leu Ile Lys Tyr Ala Ser Gln Ser Ile Ser Gly Ile Pro Ser Arg Phe Ser Gly Ser Gly
45                  50                  55                  60                  65
Ser Gly Thr Asp Phe Thr Leu Ser Ile Asn Ser Val Glu Thr Glu Asp Phe Gly Met Tyr Phe Cys
                    70                  75                  80                  85
Gln Gln Ser Asn Ser Trp Pro His Thr Phe Gly Gly Gly Thr Lys Leu Glu Ile Lys Arg Ala
                    90                  95                  100                 105

| FR 1 Vκ | Thr | Gln | Thr | Pro | Ala | Thr | Leu | Ser | Val | Thr | Pro | Gly | Asp | Ser | Val | Ser | Leu | Ser | Cys |
|---|---|---|---|---|---|---|---|---|---|---|---|---|---|---|---|---|---|---|---|
| #1 | Ser | - | - | - | - | - | - | - | - | Leu | Ser | - | Glu | Arg | Ala | Thr | - | - | - |
| #2 | Ser | - | - | - | - | - | - | - | - | Leu | Ser | - | Glu | Arg | Gly | Ser | - | - | - |
| #3 | Ser | - | - | - | - | - | - | - | - | Leu | Ser | - | Glu | Arg | Ala | Thr | - | - | - |
| #4 | Ser | - | - | - | - | - | Ser | Ser | - | Ala | Ser | Val | - | Arg | - | Thr | Ile | Thr | - |
| #5 | Ser | - | - | - | - | - | Ser | Ser | - | Ala | Ser | Val | - | * | - | Thr | Ile | Thr | - |
| #6 | Ser | - | - | - | - | - | Ser | Ser | - | Ala | Ser | Val | - | Arg | - | Thr | Ile | Thr | - |

FIGURE 3b

| CDR1 Vκ | Arg | Ala | Ser | Gln | Ser | Ile | Ser | Asn | His | Leu | His |
|---|---|---|---|---|---|---|---|---|---|---|---|
| #1 | - | - | - | - | - | Val | - | Ser | Ser | Tyr | Leu | Ala |
| #2 | - | - | - | - | - | Val | - | Ser | Ser | Phe | Leu | Ala |
| #3 | - | - | - | - | - | Val | Thr | Ser | Ser | Tyr | Leu | Ala |
| #4 | - | - | - | - | - | - | - | - | Thr | Phe | - | Asn |
| #5 | - | - | - | - | - | - | - | - | Ser | Tyr | - | Asn |
| #6 | - | - | - | - | - | - | - | - | Ser | Tyr | - | Asn |

FR2

| $V_\kappa$ | Trp | Tyr | Gln | Gln | Lys | Ser | His | Glu | Ser | Pro | Arg | Leu | Leu | Ile | Lys |
|---|---|---|---|---|---|---|---|---|---|---|---|---|---|---|---|
| #1 | – | – | – | – | – | Pro | Gly | Gln | Ala | – | – | – | – | – | Tyr |
| #2 | – | – | – | – | – | Pro | Gly | Gln | Ala | – | – | – | – | – | Tyr |
| #3 | – | – | – | – | – | Pro | Gly | Gln | Ala | – | – | – | – | – | Tyr |
| #4 | – | – | – | – | – | Pro | Gly | Lys | Ala | – | – | Lys | Phe | – | Tyr |
| #5 | – | – | – | Arg | – | Pro | Gly | Lys | Ala | – | – | Lys | Leu | – | Tyr |
| #6 | – | – | – | – | – | Pro | Gly | Lys | Ala | – | – | Lys | Leu | – | Tyr |

FIGURE 3c

CDR2

| $V_\kappa$ | Tyr | Ala | Ser | Gln | Ser | Ile | Ser |
|---|---|---|---|---|---|---|---|
| #1 | Gly | – | – | – | Ser-Arg-Ala-Thr | | |
| #2 | Gly | – | – | – | Ser-Arg-Ala-Thr | | |
| #3 | Gly | – | – | – | Ser-Arg-Ala-Thr | | |
| #4 | Ala | – | – | – | Thr Leu Gln | – | |
| #5 | Ala | – | – | – | Thr Leu Gln | – | |
| #6 | Ala | – | – | – | Thr Leu Gln | – | |

| Vκ | | | | | | | | | | | | | | | | | | | | | |
|---|---|---|---|---|---|---|---|---|---|---|---|---|---|---|---|---|---|---|---|---|---|
| | Gly | Ile | Pro | Ser | Arg | Phe | Ser | Gly | Ser | Gly | Ser | Gly | Thr | Asp | Phe | Thr | Leu | Ser | Ile | Asn | Ser |
| | Val | Glu | Thr | Glu | Asp | Phe | Gly | Met | Tyr | Phe | Cys | | | | | | | | | | |
| #1 | – | – | – | – | – | – | – | Ala | – | – | – | – | – | – | – | – | – | Ile | – | Thr | – | Ser |
| | Leu | – | Asp | – | – | – | Val | – | Tyr | – | – | | | | | | | | | | Arg |
| #2 | – | – | – | – | – | – | – | Ala | – | – | – | – | – | Val | – | – | – | – | – | Thr | – | Ser |
| | Leu | – | Asp | – | – | – | Val | – | Tyr | – | – | | | | | | | | | | Arg |
| #3 | – | – | – | – | – | – | – | Ala | – | – | – | – | – | – | – | Ile | Phe | Thr | – | – | Ser |
| | Leu | – | Asp | – | – | – | Val | – | Tyr | – | – | | | | | | | | | | Arg |
| #4 | Val | – | – | – | – | – | – | Ala | – | – | – | – | – | – | – | – | – | – | – | Thr | – | Ser |
| | Leu | Gln | Pro | – | – | – | Val | – | Tyr | – | – | | | | | | | | | | |
| #5 | Val | – | – | – | – | – | – | Ala | – | – | – | – | – | – | – | – | – | – | Ala | Thr | – | Ser |
| | Leu | Gln | Pro | – | – | – | Val | – | Tyr | – | – | | | | | | | | | | |
| #6 | Val | – | – | – | – | – | – | Ala | – | – | – | – | – | – | – | – | – | – | – | Thr | – | Ser |
| | Leu | Gln | Pro | – | – | – | Val | – | Tyr | – | – | | | | | | | | | | |

FIGURE 3e

|  | ←―――――――――――― LCDR1 ――――――――――――→ | | ←―――――― LCDR2 |
|---|---|---|---|
| mouse | Arg Ala Ser Gln Ser Ile Ser Asn | His Leu His | (Lys) Tyr Ala Ser Gln Ser Ile Ser |
| selected human | | | |
| 3 x | Arg Ala Ser Gln Asp Ile Gly Thr | Ser Leu His | (Lys) Tyr Ala Ser Gln Pro Val Phe |
| 2 x | Arg Ala Ser Gln Asp Ile Gly Asn | Ser Leu His | (Lys) Tyr Ala Ser Gln Pro Val Phe |
| 1 x | Arg Ala Ser Gln Ser Ile Gly Trp | Ser Leu His | (Lys) Tyr Ala Ser Gln Ser Ile Ser |
| unselected human | | | |
|  | Arg Ser Ser Gln Ser Ile Asn Ile | Tyr Leu Ala | (Tyr) His Ala Ser Lys Arg Ala Ser |
|  | Arg Ala Ser Val Ser Asn Asn | Tyr Leu Ala | (Tyr) Arg Ala Ser Ser Arg Ala Thr |
|  | Arg Ser Ser Gln Ser Leu Val Tyr Ser Asp Gly Asn Thr | Tyr Leu Asn | (Tyr) Lys Val Ser Asn Arg Asp Ser |
|  | Thr Ala Ser Gln Ser Leu Val Tyr Thr Asp Gly Asn Thr | Tyr Leu Ser | (Tyr) Met Val Ser Asn Arg Asp Ser |

V_L amino acid sequences

FR1
mouse
Glu Leu Val Met Thr Gln Thr Pro Ala Thr Leu Ser Val Thr Pro Gly Asp Ser Val Ser Leu Ser Cys
human (Group A)
Glu Leu Val Met Thr Gln Thr Pro Ser Pro Glu Phe Gln Ser Val Thr Pro Lys Glu Thr Val Thr Ile Thr Cys
human (Groups BCDE)
Glu Leu Val Met Thr Gln Ser Pro Glu Phe Gln Ser Val Thr Pro Lys Glu Thr Val Thr Ile Thr Cys CDR1
mouse
Arg Ala Ser Gln Ser Ile Ser Asn His Leu His
human (Group A)
Arg Ala Ser Gln Asp Ile Gly Thr Ser Leu His
human (Groups BCDE)
Arg Ala Ser Gln Asp Ile Gly Asn Ser Leu His FR2
mouse
Trp Tyr Gln Gln Lys Ser His Glu Ser Pro Arg Leu Leu Ile Lys
human (Group A)
Trp Tyr Gln Gln Lys Pro Gly Gln Ser Pro Lys Leu Leu Ile Lys
human (Groups BCDE)
Trp Tyr Gln Gln Lys Pro Gly Gln Ser Pro Lys Leu Leu Ile Lys CDR2
mouse
Tyr Ala Ser Gln Ser Ile Ser
human (Group A)
Tyr Ala Ser Gln Pro Val Phe
human (Groups BCDE)
Tyr Ala Ser Gln Pro Val Phe FIGURE 8b V$_L$ amino acid sequences FR3
mouse
Gly Ile Pro Ser Arg Phe Ser Gly Ser Gly Ser Gly Thr Asp Phe Thr Leu Ser Ile Asn Ser Val
Glu Thr Glu Asp Phe Gly Met Tyr Phe Cys
human (Group A)
Gly Val Pro Ser Arg Phe Ser Gly Ser Gly Ser Gly Thr Asp Phe Thr Leu Thr Ile Tyr Ser Leu
Glu Ala Glu Asp Phe Ala Val Tyr Tyr Cys
human (Group BCDE)
Gly Val Pro Ser Arg Phe Arg Gly Ser Gly Ser Gly Thr Asp Phe Thr Leu Thr Ile Ser Arg Leu
Glu Pro Glu Asp Phe Ala Val Tyr Tyr Cys CDR3
mouse
Gln Gln Ser Asn Ser Trp Pro His Thr
human (Group A)
Gln Gln Ser Asn Ser Trp Pro His Thr
human (Group BCDE)
Gln Gln Ser Asn Ser Trp Pro His Thr FR4
mouse
Phe Gly Gly Gly Thr Lys Leu Glu Ile Lys Arg Ala
human (Group A)
Phe Gly Gln Gly Thr Lys Leu Glu Ile Lys Arg Thr
human (Group BCDE)
Phe Gly Gln Gly Thr Lys Leu Glu Ile Lys Arg Thr

FIGURE 8c

$V_H$ amino acid sequences

FR1 mouse
Glu Val Gln Leu Glu Glu Ser Gly Gly Gly Leu Val Lys Pro Gly Gly Ser Leu Lys Leu Ser Cys
Ala Ala Ser Gly Phe Ala Phe Ser
human (Group A)
Gln Val Gln Leu Val Gln Ser Gly Ala Glu Val Arg Lys Pro Gly Ser Ser Val Arg Val Ser Cys
Lys Ala Ser Gly Thr Phe Ser
human (Group B)
Gln Val Gln Leu Gln Glu Ser Gly Pro Gly Leu Val Lys Pro Ser Gln Thr Leu Ser Leu Thr Cys
Thr Val Ser Gly Ala Ser Ile Ser
human (Group C)
Gln Val Gln Leu Gln Glu Ser Gly Pro Gly Leu Val Lys Pro Ser Gln Thr Leu Phe Leu Thr Cys
Thr Val Ser Gly Gly Ser Ile Ser
human (Group D)
Thr Val Ser Gly Gly Ser Ile Ser
human (Group D)
Gln Val Gln Leu Gln Glu Ser Gly Pro Gly Leu Val Lys Pro Ser Glu Thr Leu Ser Leu Thr Cys
Ser Val Ser Gly Gly Ser Ile Ser
human (Group E)

CDR1 mouse
Ser Tyr Asp Met Ser
human (Group A)
Gly Phe Ala Val Ser
human (Group B)
Arg Gly Gly Tyr Tyr Trp Ser
human (Group C)
Ser Gly Gly Tyr Tyr Trp Ser
human (Group D)
Ser Gly Gly Tyr Tyr Trp Ser
human (Group E)
Ser Gly Gly Tyr Tyr Trp Ser

FR2 mouse
Trp Val Arg Gln Ile Pro Glu Lys Arg Leu Glu Trp Val Ala
human (Group A)
Trp Val Arg Gln Ala Pro Gly Gln Arg Phe Glu Trp Leu Gly
human (Group B)
Trp Ile Arg Gln Tyr Pro Gly Lys Gly Leu Glu Trp Ile Gly
human (Group C)
Trp Ile Arg Gln His Pro Gly Lys Gly Leu Glu Trp Ile Gly
human (Group D)
Trp Ile Arg Gln His Pro Gly Lys Gly Leu Glu Trp Ile Gly
human (Group E)
Trp Ile Arg His His Pro Gly Lys Gly Leu Glu Trp Ile Gly FIGURE 8d $V_H$ amino acid sequences CDR2
mouse
Lys Val Ser Ser Gly Gly Gly Ser Thr Tyr Tyr Leu Asp Thr Val Gln Gly
human (Group A)
Gly Ile Val Ala Ser Leu Gly Ser Thr Asp Tyr Ala Gln Lys Phe Gln Asp
human (Group B)
Tyr Ile His          His Ser Gly Ser Thr Tyr Tyr Asn Pro Ser Leu Lys Ser
human (Group C)
Tyr Ile His          His Arg Ala Ala Pro Tyr Tyr Tyr Asn Pro Ser Leu Lys Ser
human (Group D)
Tyr Ile His          His Ser Ala Gly Thr Tyr Tyr Tyr Asn Pro Ser Leu Lys Ser
human (Group E)
Tyr Ile His          His Ser Ala Gly Thr Tyr Tyr Tyr Asn Pro Ser Leu Lys Ser FR3
mouse
Arg Phe Thr Ile Ser Arg Asp Asn Ala Lys Asn Thr Leu Tyr Leu Gln Met Ser Ser Leu Asn Ser
Glu Asp Thr Ala Met Tyr Tyr Cys Ala Arg
human (Group A)
Lys Leu Thr Ile Thr Val Asp Glu Ser Thr Ala Thr Val Tyr Met Glu Met Arg Asn Leu Arg Ser
Asp Asp Thr Ala Val Tyr Tyr Cys Ala Ar
human (Group B)
Arg Val Thr Ile Ala Ile Asp Thr Ser Lys Asn Gln Leu Ser Leu Arg Leu Arg Ser Val Thr Ala
Ala Asp Thr Ala Val Tyr Tyr Cys Ala Arg
human (Group C)
Ser Val Thr Ile Ser Val Asp Thr Ser Arg Asn Gln Ile Ser Leu Lys Leu Lys Ser Val Thr Ala
Ala Asp Thr Ala Val Tyr Tyr Cys Ala Arg
human (Group D)
Ser Val Thr Met Ser Val Asp Thr Ser Lys Asn Gln Leu Ser Leu Lys Leu Thr Ser Val Thr Ala
Ala Asp Thr Ala Val Tyr Tyr Cys Ala Arg
human (Group E)
Arg Val Thr Met Ser Ala Asp Thr Ser Lys Asn Gln Leu Ser Leu Lys Leu Ala Ser Val Thr Ala
Ala Asp Thr Ala Val Tyr Tyr Cys Ala Arg

FIGURE 8e $V_H$ amino acid sequences

CDR3 mouse
His Asn Tyr Gly Ser Phe Ala Tyr
human (Group A)
His Asn Tyr Gly Ser Phe Ala Tyr
human (Group B)
His Asn Tyr Gly Ser Phe Ala Tyr
human (Group C)
His Asn Tyr Gly Ser Phe Ala Tyr
human (Group D)
His Asn Tyr Gly Ser Phe Ala Tyr
human (Group E)
His Asn Tyr Gly Ser Phe Ala Tyr

FR4 mouse
Trp Gly Gln Gly Thr Leu Val Thr Val Ser Ala
human (Group A)
Trp Gly Gln Gly Thr Leu Val Thr Val Ser Ser
human (Group B)
Trp Gly Gln Gly Thr Leu Val Thr Val Ser Ser
human (Group C)
Trp Gly Gln Gly Thr Leu Val Thr Val Ser Ser
human (Group D)
Trp Gly Gln Gly Thr Leu Val Thr Val Ser Ser
human (Group E)
Trp Gly Gln Gly Thr Leu Val Thr Val Ser Ser

HUMANIZATION OF MURINE ANTIBODY

CROSS-REFERENCE TO RELATED APPLICATIONS

This application is a continuation of U.S. patent application Ser. No. 08/986,016 filed on Dec. 5, 1997, now abandoned.

GOVERNMENTAL RIGHTS

This invention was made with government support under Contract No. AI 37470 by the National Institutes of Health. The government has certain rights in the invention.

TECHNICAL FIELD

This invention relates to humanization of murine antibodies.

BACKGROUND OF THE INVENTION

Antibodies typically comprise two heavy chains linked together by disulfide bonds and two light chains linked to a respective heavy chain by a disulfide bond. Beginning at one end of each heavy chain there is a variable domain followed by several constant domains. Similarly, each light chain has a variable domain at one end, but only a single constant domain at its other end. There are two types of light chain, which are termed lambda ($\lambda$) and kappa ($\kappa$) chains. No functional difference has been found between antibodies having $\lambda$ or $\kappa$ light chains. The ratio of the two types of light chain varies from species to species, however. In mice, the $\kappa:\lambda$ ratio is 20:1, whereas in humans it is 2:1.

The variable domains of the light and heavy chains are aligned, as are the constant domain of the light chain and the first constant domain of the heavy chain. The constant domains in the light and heavy chains are not involved directly in binding the antibody to antigen.

It is the variable domains that form the antigen binding site of antibodies. The general structure of each light and heavy chain domain comprises a framework of four regions, whose sequences are relatively conserved, connected by three complementarity determining regions (CDRs). The four framework regions employ a beta-sheet conformation and the CDRs form loops connecting, and in some cases forming part of, the beta-sheet structure. The CDRs are held in close proximity by the framework regions and, with the CDRs from the other domain, contribute to the formation of the antigen binding site.

While cell surface antigens of tumor cells are the traditional targets for antibody-guided cancer therapy, one of the major limitations for the therapy of solid tumors is the low accessibility of tumor antigens to antibodies circulating in the blood stream. The dense packing of tumor cells and the elevated interstitial pressure in the tumor core present formidable physical barriers.

A solution to the problem of poor penetration of antibodies into solid tumors would be to attack the endothelial cells lining the blood vessels of the tumor rather than the tumor cells themselves. While it may be difficult to target the mature tumor vasculature specifically, i.e., without destroying healthy tissue, promising strategies aim at the inhibition of neovascularization.

Neovascularization, also termed angiogenesis, is induced by cytokines that are secreted from tumor cells and depends on vascular cell migration and invasion, processes regulated by cell adhesion molecules (CAM) and protease. These molecules are currently considered potential targets for angiogenic inhibitors. In this regard, the vascular integrin $\alpha_v\beta_3$ has recently been identified as a marker of angiogenic blood vessels. See Brooks, P. C., et al. (1994), REQUIREMENT OF INTEGRIN $\alpha_v\beta_3$ FOR ANGIOGENESIS, *Science* 264, 569–571. Moreover, it was shown that the mouse monoclonal antibody (Mab) LM609 directed to integrin $\alpha_v\beta_3$ was able to suppress angiogenesis, indicating than integrin $\alpha_v\beta_3$ has a critical role in angiogenesis.

It has been further demonstrated that LM609 selectively promotes apoptosis of vascular cells that have been stimulated to undergo angiogenesis. See Brooks, P. C., et al. (1994), INTEGRIN $\alpha_v\beta_3$ ANTAGONISTS PROMOTE TUMOR REGRESSION BY INDUCING APOPTOSIS OF ANGIOGENIC BLOOD VESSELS, *Cell* 79, 1157–1164. These findings suggest that integrin $\alpha_v\beta_3$ may be a target and LM609 a tool for cancer diagnosis and therapy.

Indeed, LM609 not only prevented the growth of histologically distinct human tumors implanted on the chorioallantoic membranes of chicken embryos, but also induced their regression. See, *Cell* 79, 1157–1164. Using a more clinically relevant model of tumor growth, it was found that LM609 blocked human breast cancer growth in a SCID mouse/human chimeric model. Importantly, not only did LM609 block tumor growth, but it also inhibited metastasis of the breast carcinomas examined. See Brooks, et al. (1995) ANTI-INTEGRIN $\alpha_v\beta_3$ BLOCKS HUMAN BREAST CANCER GROWTH AND ANGIOGENESIS IN HUMAN SKIN, *J. Clin. Invest.* 96, 1815–1822.

The Brooks et al. results are consistent with previous studies that have suggested that angiogenesis contributes to the metastatic spread of breast tumor cells. See Weidner, N., et al. (1991) TUMOR ANGIOGENESIS AND METASTASIS: CORRELATION IN INVASIVE BREAST CARCINOMA, *N. Engl. J. Med.* 324, 1–8; and Weidner, N., et al. (1992) TUMOR ANGIOGENESIS: A NEW SIGNIFICANT AND INDEPENDENT PROGNOSTIC INDICATOR IN EARLY-STAGE BREAST CARCINOMA, *J.Natl. Cancer Inst.* 84, 1875–1887.

Within the last few years evidence has been presented that two cytokine-dependent pathways of angiogenesis exist and that these are defined by their dependency on distinct vascular integrins. See Friedlander, M., et al. (1995) DEFINITION OF TWO ANGIOGENIC PATHWAYS BY DISTINCT AV INTEGRINS, *Science* 270, 1500–1502. The results of the Friedlander et al. studies show that anti-$\alpha_v\beta_3$ antibody LM609 blocked angiogenesis in response to bFGF and TNF$\alpha$, yet have little effect on angiogenesis induced by VEGF, TGF$\alpha$, or phorbol ester PMA. In contrast, the anti-$\alpha_v\beta_5$ antibody P1F6 blocks angiogenesis induced by VEGF, TGF$\alpha$, and phorbol ester PMA, while having minimal effects on that induced by bFGF or TNF$\alpha$.

It is conceivable, thus, that tumors showing less susceptibility to anti-$\alpha_v\beta_3$ antibodies might secrete cytokines that promote angiogenesis in an $\alpha_v\beta_5$-dependent manner. Taken together, both anti-$\alpha_v\beta_3$ and anti-$\alpha_v\beta_5$ antibodies are promising tools for diagnosis and therapy of cancer.

Mouse monoclonal antibodies such as LM609, however, are highly immunogenic in humans, thus limiting their potential use for cancer therapy, especially when repeated administration is necessary. To reduce the immunogenicity of mouse monoclonal antibodies, chimeric monoclonal antibodies were generated, with the variable Ig domains of a mouse monoclonal antibody being fused to human constant Ig domains. See Morrison, S. L., et al. (1984) CHIMERIC HUMAN ANTIBODY MOLECULES; MOUSE ANTIGEN-BINDING DOMAINS WITH HUMAN CONSTANT REGION DOMAINS, *Proc. Natl. Acad. Sci. USA* 81, 6841–6855; and, Boulianne, G. L., et al.

(1984) PRODUCTION OF A FUNCTIONAL CHIMAERIC MOUSE/HUMAN ANTIBODY, *Nature* 312, 643–646. This process is commonly referred to as "humanization" of an antibody.

In general, the chimeric monoclonal antibodies retain the binding specificity of the mouse monoclonal antibody and exhibit improved interactions with human effector cells. This results in an improved antibody-dependent cellular cytotoxicity which is presumed to be one of the ways of eliminating tumor cells using monoclonal antibodies. See Morrison, S. L. (1992) IN VITRO ANTIBODIES: STRATEGIES FOR PRODUCTION AND APPLICATION, *Ann. Rev. Immunol.* 10, 239–265. Though some chimeric monoclonal antibodies have proved less immunogenic in humans, the mouse variable Ig domains can still lead to a significant human antimouse response. See Bruggemann, M., et al. (1989) THE IMMUNOGENICITY OF CHIMERIC ANTIBODIES, *J. Exp. Med.* 170, 2153–2157. Therefore, for therapeutic purposes it may be necessary to fully humanize a murine monoclonal antibody by altering both the variable and the constant Ig domains.

Full humanization is feasible by introducing the six CDRs from the mouse heavy and light chain variable Ig domains into the appropriate framework regions of human variable Ig domains. This CDR grafting technique (Riechmann, L., et al. (1988) RESHAPING HUMAN ANTIBODIES FOR THERAPY, *Nature* 332, 323) takes advantage of the conserved structure of the variable Ig domains, with the four framework regions (FR1–FR4) serving as a scaffold to support the CDR loops which are the primary contacts with antigen. U.S. Pat. No. 5,502,167 to Waldmann, et al. discloses a "humanised antibody" having the CDR loops LCDR1 through LCDR3 and HCDR1 through HCDR3 from YTH 655(5)6, a rat IgG2b monoclonal antibody, grafted onto a human T cell antibody.

A drawback, however, of the CDR grafting technique is the fact that amino acids of the framework regions can contribute to antigen binding, as well as amino acids of the CDR loops can influence the association of the two variable Ig domains. To maintain the affinity of the humanized monoclonal antibody, the CDR grafting technique relies on the proper choice of the human framework regions and site-directed mutagenesis of single amino acids aided by computer modeling of the antigen binding site (e.g., Co, M. S., et al. (1994) A HUMANIZED ANTIBODY SPECIFIC FOR THE PLATELET INTEGRIN gpllb/lla, *J. Immunol.* 152, 2968–2976). A number of successful humanizations of mouse monoclonal antibodies by rational design have been reported. Among them are several monoclonal antibodies that are directed to human integrins and have potential clinical application. See, *J. Immunol.* 152, 2968–2976; Hsiao, K. C., et al. (1994) HUMANIZATION OF 60.3, AN ANTI-CD18 ANTIBODY; IMPORTANCE OF THE L2 LOOP, *Protein Eng.* 7, 815–822; and, Poul, M. A., et al. (1995) INHIBITION OF T CELL ACTIVATION WITH A HUMANIZED ANTI-BETA 1 INTEGRIN CHAIN mAb, *Mol. Immunol.* 32, 101–116.

Human immunoglobulin transgenic mice provide a promising alternative to the humanization of mouse monoclonal antibodies. See, e.g., Fishwild, D. M., et al. (1996) HIGH-AVIDITY HUMAN IgGk MONOCLONAL ANTIBODIES FROM A NOVEL STRAIN OF MINILOCUS TRANSGENIC MICE, *Nature Biotechnology* 14, 845–851. In response to immunization, these mice express human monoclonal antibodies, which can be accessed by conventional hybridoma technology.

Rational design strategies in protein engineering have been challenged by in vitro selection strategies that are mainly based on phage display libraries. See Clackson, T., and Wells, J. A. (1994) IN VITRO SELECTION FROM PROTEIN AND PEPTIDE LIBRARIES, *TIBTECH* 12, 173–184. In particular, in vitro selection and evolution of antibodies derived from phage display libraries has become a powerful tool. See Burton, D. R., and Barbas III, C. F. (1994) HUMAN ANTIBODIES FROM COMBINATORIAL LIBRARIES, *Adv. Immunol.* 57, 191–280; and, Winter, G., et al. (1994) MAKING ANTIBODIES BY PHAGE DISPLAY TECHNOLOGY, *Annu. Rev. Immunol.* 12, 433–455.

The development of technologies for making repertoires of human antibody genes, and the display of the encoded antibody fragments on the surface of filamentous bacteriophage, has provided a means for making human antibodies directly. The antibodies produced by phage technology are produced as antigen binding fragments—usually Fv or Fab fragments—in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Typically, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. By several rounds of antigen binding and reamplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody. See Jespers, L. S., et al. (1994) GUIDING THE SELECTION OF HUMAN ANTIBODIES FROM PHAGE DISPLAY REPERTOIRES TO A SINGLE EPITOPE OF AN ANTIGEN, *Bio/Technology* 12, 899–903. For this, the Fd fragment of the mouse monoclonal antibody can be displayed in combination with a human light chain library, and the resulting hybrid Fab library may then be selected with antigen. The mouse Fd fragment thereby provides a template to guide the selection.

Subsequently, the selected human light chains are combined with a human Fd fragment library. Selection of the resulting library yields entirely human Fab.

For the full humanization of murine monoclonal antibodies, the present invention uses a unique combination of CDR grafting and guided selection. The anti-integrin antibody generated is useful for cancer diagnosis and therapy.

SUMMARY Of THE INVENTION

Humanization of a mouse monoclonal antibody is achieved by a combination of guided selection and CDR grafting. The term "humanized" as used herein and in the appended claims means that at least one chain of a mouse monoclonal antibody includes a region of a human monoclonal antibody.

A humanized mouse monoclonal antibody is produced by constructing a library of human antibody heavy chains or light chains in which each such chain includes a variable domain and has at least one complementarity determining region (CDR) amino acid sequence which is that of a corresponding mouse heavy or light antibody chain, and then combining the library so constructed with a complementary chain from an antibody which binds a preselected antigen. In this manner, the complementary chain together with a human chain present in the constructed library forms a heavy and light chain pair in a resulting library of humanized chain pairs. Thereafter a particular humanized heavy and light chain pair is selected from the humanized pair library using the aforementioned complementary chain.

In a particular embodiment, a mouse monoclonal antibody can be humanized by constructing a human light chain library in which each light chain includes at least the variable domain thereof and at least one CDR amino acid sequence of a mouse light chain, and a human heavy chain library in which each such heavy chain includes at least the variable domain thereof and at least one CDR amino acid sequence of a mouse heavy chain. The heavy chain usually is no more than about 200 amino acid residues in size.

A human light chain having a mouse CDR is selected from the constructed human light chain library using a heavy chain from an antibody which binds a preselected antigen. The constructed heavy chain library is combined with the selected human light having a mouse CDR to produce a humanized library of heavy and light chain pairs, each containing at least one mouse CDR. Thereafter, a heavy and light chain pair with mouse CDR is selected from the aforesaid humanized library using the selected human light chain with mouse CDR. The sequence of aforementioned library construction is not critical.

Preferably, only the light chain complementarity determining region three (LCDR3) loop of the monoclonal antibody is grafted onto the human light chain. Similarly, it is preferable that only the HCDR3 loop be grafted onto the human heavy chain (HC) fragment. The selection of either the human light chain or human heavy chain having the grafted mouse CDR is preferably made by using a chimeric mouse/human complementary chain as a template.

In CDR grafting onto a human light chain, the human light chain is cloned, then the clones are randomly recombined to form a library such as a combinatorial phage display library. The same method can be followed for grafting onto the human heavy chain.

BRIEF DESCRIPTION OF THE DRAWINGS

FIGS. 2a and 2b show the amino acid sequences of $V_\lambda$ (SEQ ID NO: 44) and $V_\kappa$ (SEQ ID NO: 45), respectively, of mouse monoclonal antibody LM609. The N-terminal two amino acids (Leu)(Glu) of V and (Glu)(Leu) of V encoded by the vector cloning sites CTCGAG (XhoI) and GAGCTC (SacI), respectively, are artificial. The CDR loops are underlined.

FIG. 3a through FIG. 3e show the amino acid sequence alignment of mouse LM609 $V_\kappa$ (top full line of each sequence grouping) and six selected human $V_\kappa$'s (#1–6). Framework regions (FR1–3) and CDR (CDR1–2) loops are separated. Lines (-) indicate identical amino acids. Note that due to the LCDR3 grafting parts of FR3, entire CDR3 and entire FR4 are identical in mouse LM609 $V_\kappa$ and the selected human $V_\kappa$'s. Therefore, these two sequences are not shown.

In FIG. 3a, the top line (labeled "$V_\kappa$") represents amino acid residues 5–23 of SEQ ID NO: 45. The lines labeled "#1" and "#3" each represent amino acid residues of human $V_\kappa$ clones having Ser in alignment with Thr7 of SEQ ID NO: 45, Gly-Thr in alignment with Ala9-Thr10 of SEQ ID NO: 45, Leu-Ser in alignment with Val13-Thr14 of SEQ ID NO: 45, and Glu-Arg-Ala-Thr (SEQ ID NO: 57) in alignment with Asp17-Ser18-Val19-Ser20 of SEQ ID NO: 45. The line labeled "#2" represents amino acid residues of a human $V_\kappa$ clone having Ser in alignment with Thr7 of SEQ ID NO: 45, Gly-Thr in alignment with Ala9-Thr10 of SEQ ID NO: 45, Leu-Ser in alignment with Val13-Thr14 of SEQ ID NO: 45, and Glu-Arg-Gly-Ser (SEQ ID NO: 58) in alignment with Asp17-Ser18-Val19-Ser20 of SEQ ID NO: 45. The lines labeled "#4" and "#6" each represent amino acid residues of a human $V_\kappa$ clone having Ser in alignment with Thr7 of SEQ ID NO: 45, Ser-Ser in alignment with Ala9-Thr10 of SEQ ID NO: 45, Ala-Ser-Val in alignment with Val13-Thr14-Pro15 of SEQ ID NO: 45, Arg in alignment with Ser18 of SEQ ID NO: 45, and Thr-Ile-Thr in alignment with Ser20-Leu21-Ser22 of SEQ ID NO: 45. The line labeled "#5" represents amino acid residues of a human $V_\kappa$ clone having Ser in alignment with Thr7 of SEQ ID NO: 45, Ser-Ser in alignment with Ala9-Thr10 of SEQ ID NO: 45, Ala-Ser-Val in alignment with Val13-Thr14-Pro15 of SEQ ID NO: 45, and Thr-Ile-Thr in alignment with Ser20-Leu21-Ser22 of SEQ ID NO: 45.

In FIG. 3b, the top line (labeled "$V_\kappa$") represents amino acid residues 24–34 of SEQ ID NO: 45. The line labeled "#1" represents amino acid residues of a human $V_\kappa$ clone having Val in alignment with Ile29 of SEQ ID NO: 45, and Ser-Ser-Thr-Leu-Ala (SEQ ID NO: 59) in alignment with Asn31-His32-Leu33-His34 of SEQ ID NO: 45. The line labeled "#2" represents amino acid residues of a human $V_\kappa$ clone having Val in alignment with Ile29 of SEQ ID NO: 45, and Ser-Ser-Phe-Leu-Ala (SEQ ID NO: 60) in alignment with Asn31-His32-Leu33-His34 of SEQ ID NO: 45. The line labeled "#3" represents amino acid residues of a human $V_\kappa$ clone having Val-Thr-Ser-Ser-Tyr-Leu-Ala (SEQ ID NO: 61) in alignment with Ile29-Ser30-Asn31-His32-Leu33-His34 of SEQ ID NO: 45. The line labeled "#4" represents amino acid residues of a human $V_\kappa$ clone having Thr-Phe in alignment with Asn31-His32 of SEQ ID NO: 45, and Asn in alignment with His34 of SEQ ID NO: 45. The lines labeled "#5" and "#6" each represent amino acid residues of human $V_\kappa$ clones having Ser-Tyr in alignment with Asn31-His32 of SEQ ID NO: 45, and Asn in alignment with His34 of SEQ ID NO: 45.

In FIG. 3c, the top line (labeled "$V_\kappa$") represents amino acid residues 35–49 of SEQ ID NO: 45. The lines labeled "#1", "#2", and "#3" each represent amino acid residues of human $V_\kappa$ clones having Pro-Gly-Gln-Ala (SEQ ID NO: 62) in alignment with Ser40-His41-Glu42-Ser43 of SEQ ID NO: 45 and Tyr in alignment with Lys49 of SEQ ID NO: 45. The line labeled "#4" represents amino acid residues of a human $V_\kappa$ clone having Pro-Gly-Lys-Ala (SEQ ID NO: 63) in alignment with Ser40-His41-Glu42-Ser43 of SEQ ID NO: 45, Lys-Phe in alignment with Arg45-Leu46 of SEQ ID NO: 45, and Tyr in alignment with Lys49 of SEQ ID NO: 45. The line labeled "#5" represents amino acid residues of a human $V_\kappa$ clone having Arg in alignment with Gln38 of SEQ ID NO: 45, Pro-Gly-Lys-Ala (SEQ ID NO: 63) in alignment with Ser40-His41-Glu42-Ser43 of SEQ ID NO: 45, Lys-Leu in alignment with Arg45-Leu46 of SEQ ID NO: 45, and Tyr in alignment with Lys49 of SEQ ID NO: 45. The line labeled "#6" represents amino acid residues of a human $V_\kappa$ clone having Pro-Gly-Lys-Ala (SEQ ID NO: 63) in alignment with Ser40-His41-Glu42-Ser43 of SEQ ID NO: 45, Lys-Leu in alignment with Arg45-Leu46 of SEQ ID NO: 45, and Tyr in alignment with Lys49 of SEQ ID NO: 45.

In FIG. 3d, the top line (labeled "$V_\kappa$") represents amino acid residues 50–56 of SEQ ID NO: 45. The lines labeled "#1", "#2", and "#3" each represent amino acid residues of human $V_\kappa$ clones having Gly in alignment with Tyr50 of SEQ ID NO: 45, and Ser-Arg-Ala-Thr (SEQ ID NO: 64) in alignment with Gln53-Ser54-Ile55-Ser56 of SEQ ID NO: 45. The lines labeled "#4", "#5" and "#6" each represent amino acid residues of human $V_\kappa$ clones having Ala in alignment with Tyr50 of SEQ ID NO: 45, and Thr-Leu-Gln in alignment with Gln53-Ser54-Ile55 of SEQ ID NO: 45.

In FIG. 3e, the top 2 lines (labeled "$V_\kappa$") represent amino acid residues 57–88 of SEQ ID NO: 45. The lines labeled "#1" represent amino acid residues of a human $V_\kappa$ clone having Asp in alignment with Ser60 of SEQ ID NO: 45, Ile in alignment with Thr72 of SEQ ID NO: 45, Thr in alignment with Ser74 of SEQ ID NO: 45, Ser-Arg-Leu in alignment with Asn76-Ser77-Val78 of SEQ ID NO: 45, Pro in alignment with Thr80 of SEQ ID NO: 45, Ala-Val in alignment with Gly84-Met85 of SEQ ID NO: 45, and Tyr in alignment with Phe87 of SEQ ID NO: 45. The lines labeled "#2" represent amino acid residues of a human $V_\kappa$ clone having Asp in alignment with Ser60 of SEQ ID NO: 45, Val in alignment with Asp70 of SEQ ID NO: 45, Thr in alignment with Ser74 of SEQ ID NO: 45, Ser-Arg-Leu in alignment with Asn76-Ser77-Val78 of SEQ ID NO: 45, Pro in alignment with Thr80 of SEQ ID NO: 45, Ala-Val in alignment with Gly84-Met85 of SEQ ID NO: 45, and Tyr in alignment with Phe87 of SEQ ID NO: 45. The lines labeled "#3" represent amino acid residues of a human $V_\kappa$ clone having Asp in alignment with Ser60 of SEQ ID NO: 45, Ile-Phe-Thr in alignment with Thr72-Leu73-Ser74 of SEQ ID NO: 45, Ser-Arg-Leu in alignment with Asn76-Ser77-Val78 of SEQ ID NO: 45, Pro in alignment with Thr80 of SEQ ID NO; 45, Ala-Val in alignment with Gly84-Met85 of SEQ ID NO: 45, and Tyr in alignment with Phe87 of SEQ ID NO: 45. The lines labeled "#4" and "#6" each represent amino acid residues of human $V_\kappa$ clones having Val in alignment with Ile58 of SEQ ID NO: 45, Thr in alignment with Ser74 of SEQ ID NO: 45, Ser in alignment with Asn76 of SEQ ID NO: 45, Leu-Gln-Pro in alignment with Val78-Glu79-Thr80 of SEQ ID NO: 45, Ala-Val in alignment with Gly84-Met85 of SEQ ID NO: 45, and Tyr in alignment with Phe87 of SEQ ID NO: 45. The lines labeled "#5" represent amino acid residues of a human $V_\kappa$ clone having Val in alignment with Ile58 of SEQ ID NO: 45, Ala in alignment with Gly68 of SEQ ID NO: 45, Thr in alignment with Ser74 of SEQ ID NO: 45, Ser in alignment with Asn76 of SEQ ID NO: 45, Leu-Gln-Pro in alignment with Val78-Glu79-Thr80 of SEQ ID NO: 45, Ala-Val in alignment with Gly84-Met85 of SEQ ID NO: 45, and Tyr in alignment with Phe87 of SEQ ID NO: 45.

FIG. 4 shows a comparison of three selected human fragment sequences and four unselected human fragment sequences to the original sequences of the mouse LCDR1 and LCDR2 loops.

In FIG. 4, the top sequence line shows portions of the mouse LCDR1 and LCDR2 loops, i.e., Arg-Ala-Ser-Gln-Ser-Ile-Ser-Asn (SEQ ID NO: 65) and His-Leu-His in the LCDR1 loop, and Lys-Tyr-Ala-Ser-Gln-Ser-Ile-Ser (SEQ ID NO: 66) in the LCDR2 loop. The second sequence line shows a selected human sequence in which a first portion (SEQ ID NO: 67) is in alignment with SEQ ID NO: 65 of the mouse LCDR1 loop, a second portion (Ser-Leu-His) in alignment with His-Leu-His in the mouse LCDR1 loop, and the LCDR2 loop comprises SEQ ID NO: 68. The third sequence line shows a selected human sequence in which a first portion (SEQ ID NO: 69) is in alignment with SEQ ID NO: 65 of the mouse LCDR1 loop, a second portion (Ser-Leu-His) in alignment with His-Leu-His in the mouse LCDR1 loop, and the LCDR2 loop comprises SEQ ID NO: 68. The fourth sequence line shows a selected human sequence in which a first portion (SEQ ID NO:70) is in alignment with SEQ ID NO: 65 of the mouse LCDR2 loop, a second portion (Ser-Leu-His) in alignment with His-Leu-His in the mouse LCDR1 loop, and the LCDR2 loop comprises SEQ ID NO: 71. The fifth sequence line shows an unselected human sequence in which a first portion (SEQ ID NO: 72) is in alignment with SEQ ID NO: 65 of the mouse LCDR1 loop, a second portion (Thr-Leu-Ala) in alignment with His-Leu-His in the mouse LCDR1 loop, and the LCDR2 loop comprises SEQ ID NO: 73. The sixth sequence line shows an unselected human sequence in which a first portion (SEQ ID NO: 74) is in alignment with SEQ ID NO: 65 of the mouse LCDR1 loop, a second portion (Thr-Leu-Ala) in alignment with His-Leu-His in the mouse LCDR1 loop, and the LCDR2 loop comprises SEQ ID NO: 75. The seventh sequence line shows an unselected human sequence in which a first portion (SEQ ID NO: 76) is in alignment with SEQ ID NO: 65 of the mouse LCDR1 loop, a second portion (Thr-Leu-Ala) in alignment with His-Leu-His in the mouse LCDR1 loop, and the LCDR2 loop comprises SEQ ID NO: 77. The eighth sequence line shows an unselected human sequence in which a first portion (SEQ ID NO: 78) is in alignment with SEQ ID NO: 65 of the mouse LCDR1 loop, a second portion (Thr-Leu-Ala) in alignment with His-Leu-His in the mouse LCDR1 loop, and the LCDR2 loop comprises SEQ ID NO: 79.

In FIG. 7, QQSNSWPHT is SEQ ID NO: 2, HNYGSFAY is SEQ ID NO: 1, QQXXXXPHT is SEQ ID NO: 121, and XXXXS-FAY is SEQ ID NO: 122.

FIGS. 8a and 8b are fragmented illustrations of the $V_L$ amino acid sequences of a mouse antibody compared to the amino acid sequences of five versions of humanized clones represented by group letters A (clones 10, 11, and 37), and B (clones 7, 8, and 22), C (clones 4, 31, and 36), D (clones 24, 34, 35, and 40), and E (clone 2) which are combined. In FIG. 8a, the mouse FR1 region is SEQ ID NO: 80; the human Group A and Group BCDE FR1 regions are each SEQ ID NO: 81; the mouse CDR1 region is SEQ ID NO: 82; the human Group A CDR1 region is SEQ ID NO: 83; the human Group BCDE CDR1 regions are each SEQ ID NO: 84; the mouse FR2 region is SEQ ID NO: 85; the human Group A and Group BCDE FR2 regions are each SEQ ID NO: 86; the mouse CDR2 region is SEQ ID NO: 87; and the human Group A and Group BCDE CDR2 regions are each SEQ ID NO: 88. In FIG. 8b, the mouse FR3 region is SEQ ID NO: 89; the human Group A FR3 region is SEQ ID NO: 90; the human Group BCDE FR3 regions are each SEQ ID NO: 91; the mouse CDR3 region, as well as the human Group A and human Group BCDE CDR3 regions, are each SEQ ID NO: 2; the mouse FR4 region is SEQ ID NO: 92; while the human Group A and human Group BCDE FR4 regions are each SEQ ID NO: 93.

FIGS. 8c through 8e are fragmented illustrations of the $V_H$ amino acid sequences of a mouse antibody compared to the amino acid sequences of five versions of humanized clones represented by group letters A (clones 10, 11, and 37), B (clones 7, 8, and 22), C (clones 4, 31, and 36), D (clones 24, 34, 35, and 40), and E (clone 2).

In FIG. 8c, the mouse FR1 region is SEQ ID NO: 94; the human Group A FR1 region is SEQ ID NO: 95; the human Group B FR1 region is SEQ ID NO: 96; the human Group C FR1 region is SEQ ID NO: 97; the human Group D FR1 region is SEQ ID NO: 98; the human Group E FR1 region is SEQ ID NO: 99; the mouse CDR1 region is SEQ ID NO: 100; the human Group A CDR1 region is SEQ ID NO: 101; the human Group B CDR1 region is SEQ ID NO: 102; the human Group C, D, and E CDR1 regions are each SEQ ID NO: 103; the mouse FR2 region is SEQ ID NO: 104; the human Group A FR2 region is SEQ ID NO: 105; the human Group B FR2 region is SEQ ID NO: 106; the human Group C and E FR2 regions are each SEQ ID NO: 107; and the human Group D FL2 region is SEQ ID NO: 108.

In FIG. 8d, the mouse CDR2 region is SEQ ID NO: 108; the human Group A CDR2 region is SEQ ID NO: 109; the human Group B CDR2 region is SEQ ID NO: 110; the human Group C CDR2 region is SEQ ID NO: 111; the human Group D and Group E CDR2 regions are both SEQ ID NO: 112; the mouse FR3 region is SEQ ID NO: 113; the human Group A FR3 region is SEQ ID NO: 114; the human Group B FR3 region is SEQ ID NO: 115; the human Group C FR3 region is SEQ ID NO: 116; the human Group D FR3 region is SEQ ID NO: 117; and the human Group E FR3 region is SEQ ID NO: 118.

In FIG. 8e, the mouse CDR3 region, as well as the human Group A, B, C, D and E CDR3 regions are each SEQ ID NO: 1; the mouse FR2 region is SEQ ID NO: 119, while the human Group A, B, C, D, and E FR2 regions are each SEQ ID NO: 120.

DESCRIPTION OF A PREFERRED EMBODIMENT

Figure 1:
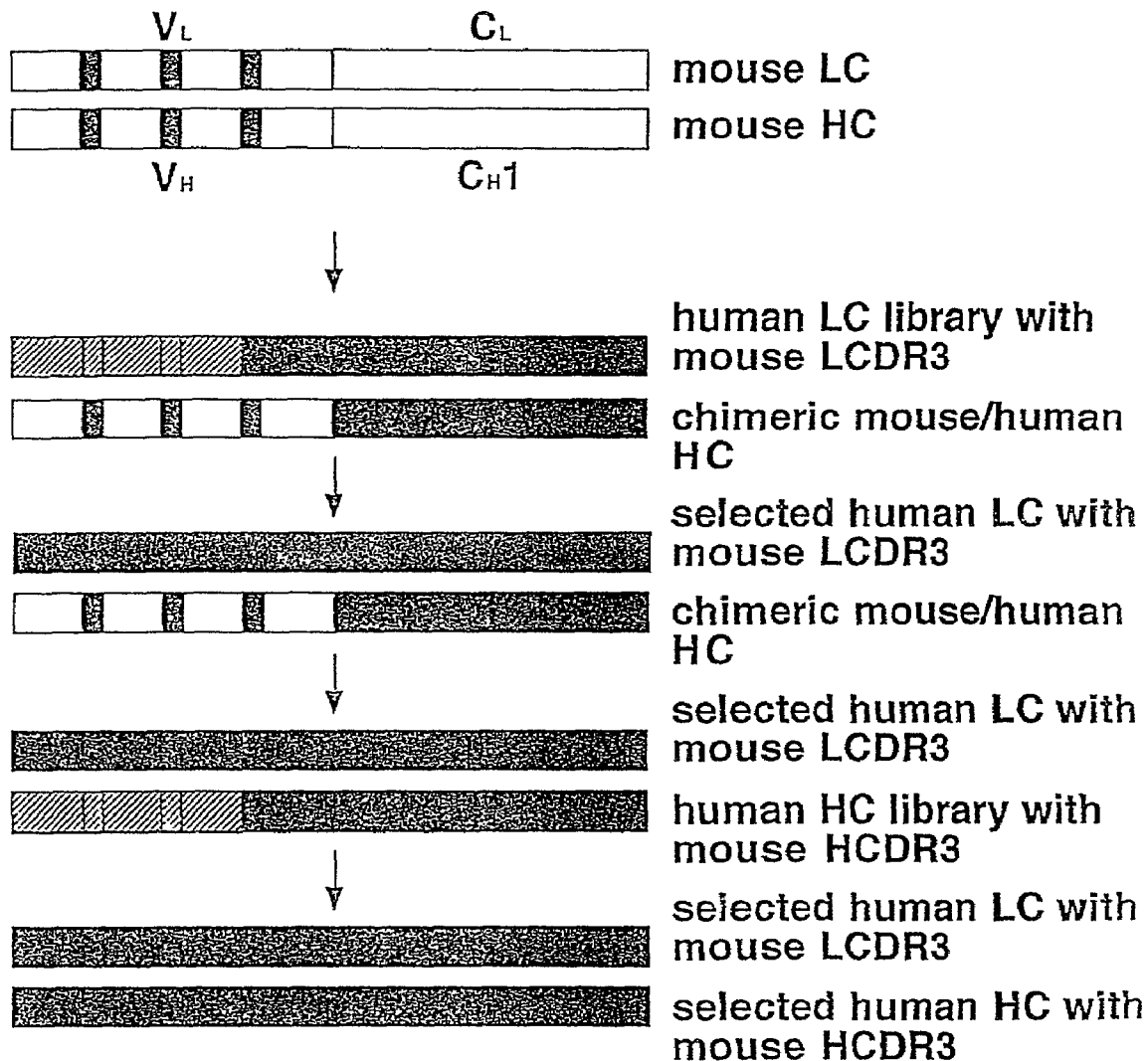
FIG. 1 is a schematic illustration showing the sequence of the steps in the combined CDR grafting technique and guided selection technique to form the humanized Fab fragment.
Figure 5A:
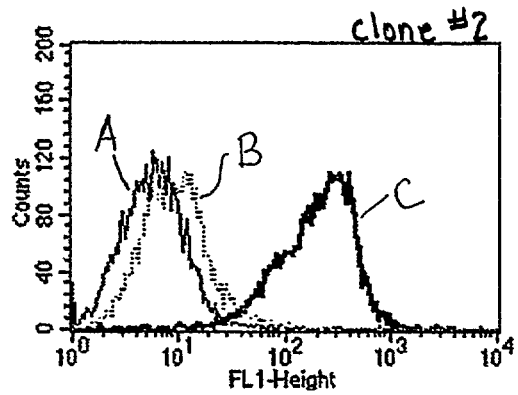
FIG. 5a through FIG. 5f are line graphs which show the binding of human integrin $\alpha_V\beta_3$ on the cell surface by humanized LM609 clones 2, 4, 7, 11, 24, and control antibody, respectively. Line A indicates untransfected CS-1 hamster cells; Line B indicates human $\gamma_5$ cDNA transfected CS-1 hamster cells (essentially the same line as line A in FIG. 5f); and line C indicates human $\beta_3$ cDNA transfected CS-1 hamster cells.
Figure 5B:
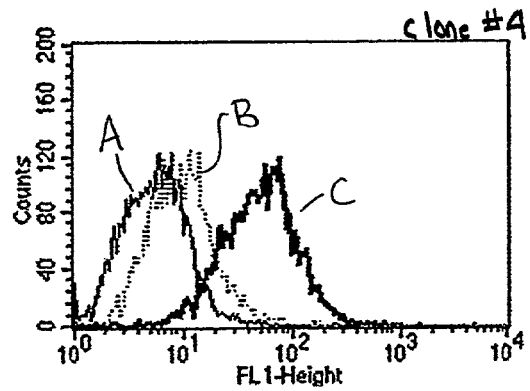
Figure 5C:
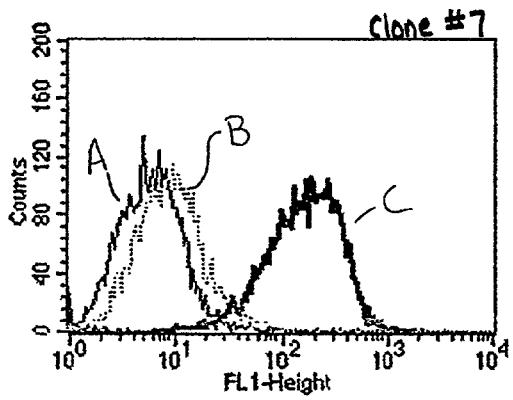
Figure 5D:
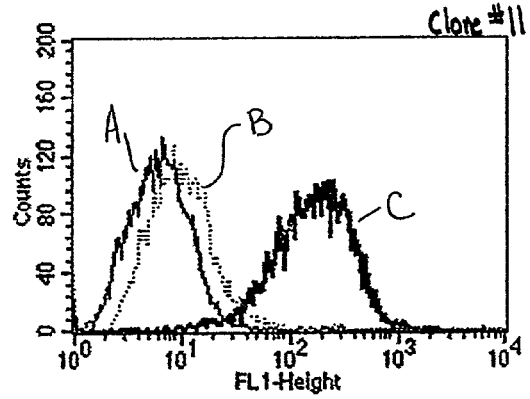
Figure 5E:
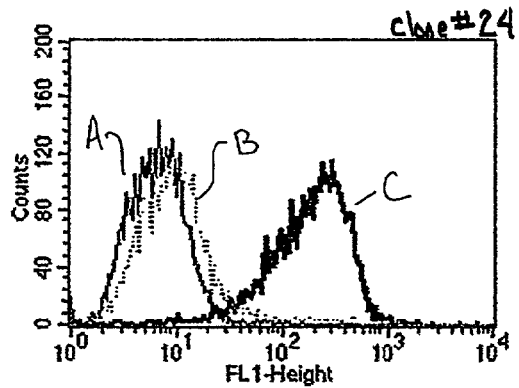
Figure 5F:
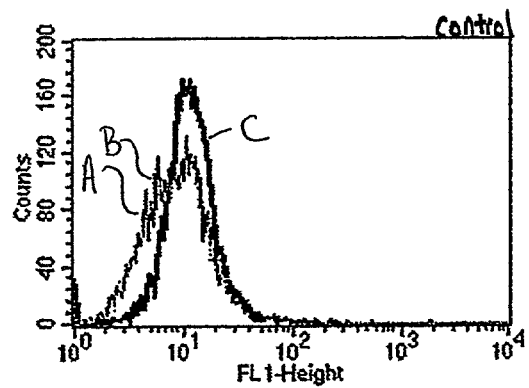

While the present invention is susceptible to embodiments in many different forms, a preferred embodiment of the invention is described below. It should be understood, however, that the present disclosure is to be considered as an exemplification of the principles of the invention and is not intended to limit the invention to the specific embodiments illustrated.

cDNA Cloning of Mouse Monoclonal Antibody LM609

Beginning with a LM609 hybridoma cell line (Deposited at and accepted by American Type Culture Collection, 10801 University Boulevard, Manassas. Va. 20110-2209. USA on Sep. 15, 1987; ATCC Designation HR 9537), total RNA was prepared from $10^8$ LM609 hybridoma cells using an RNA Isolation Kit (Stratagene, La Jolla, Calif.); Reverse transcription and polymerase chain reaction (PCR) amplification of Fd fragment and κ chain encoding sequences were performed essentially as described in "Combinatorial immunoglobulin libraries in phage 1", (*Methods* 2, 119 (1991)) by A. S. Kang, et al.

Fd fragment and κ chain encoding PCR products were cut with XhoI/SpeI and SacI/XbaI, respectively, and ligated sequentially into the appropriately digested phagemid vector pComb3H. The ligation products were introduced into *E. coli* strain XL1-Blue by electrotransformation and subsequent steps were as described in "Assembly of combinatorial antibody libraries on phage surfaces: the gene III site", (*Proc. Natl. Acad. Sci. USA* 88, 7978–7982) by C. F. Barbas III, et al., to produce phage displaying Fab on their surface. Phage were selected by panning against immobilized integrin $α_V β_3$. After two panning rounds single clones were analyzed for LM609 Fab expression. Supernatant from IPTG-induced cultures was tested for binding to immobilized integrin $α_V β_3$ by enzyme-linked immunosorbent assay (ELISA) using goat anti-mouse F(ab')$_2$ conjugated to alkaline phosphatase as a secondary antibody. The sequence of each Fd fragment and each κ chain encoding sequence of positive clones was determined by DNA sequencing.

Amplification of Human Light Chain and Fd Fragment Sequences

Total RNA was prepared from the bone marrow of five donors (Poietic Technologies; Germantown, Md.) using TRI Reagent (Molecular Research Center; Cincinnati, Ohio) and was further purified by lithium chloride precipitation. See Sambrook, J., et al. (1989) MOLECULAR CLONING: A LABORATORY MANUAL, Cold Spring Harbor Laboratory, Cold Spring Harbor, N.Y. First-strand cDNA was synthesized using the 'SUPERSCRIPT Preamplification System for First Strand cDNA Synthesis' kit with oligo (dT) priming (Life Technologies; Gaithersburg, Md.). The five generated first-strand cDNAs were subjected to separate PCR amplifications.

$V_κ$ sequences of each of the first-strand cDNAs were amplified in eight separate reactions by combining four sense and two antisense primers (see list below). $V_λ$ sequences were amplified in nine separate reactions using nine sense and one antisense primer (see list below). The $V_λ$ and $V_κ$ amino acid sequences, including the underlining of the CDR loops, are shown in FIGS. 2a and 2b, respectively (See also, SEQ ID NO:44 and SEQ ID NO:45, respectively).

$V_H$ sequences (See SEQ ID NO:56) were amplified in four reactions using four sense and one antisense primer (see list below). All amplifications were performed under standard PCR conditions using Taq polymerase (Pharmacia; Uppsala, Sweden). While the sense primers hybridize to sequences that encode the N-terminal amino acids of the various $V_κ$, $V_λ$, and $V_H$ families, the antisense primers hybridize to a sequence that encodes the C-terminal amino acids of FR3 of $V_κ$, $V_λ$, or $V_H$, respectively, which are highly conserved.

The list of primers used for the amplification of human antibody sequences include:

| $V_k$ sense primers: | |
|---|---|
| HSCK1 - F | SEQ ID NO:3 |
| HSCK24 - F | SEQ ID NO:4 |
| HSCK3 - F | SEQ ID NO:5 |
| HSCK5 - 5 | SEQ ID NO:6 |
| $V_K$ antisense primers: | |
| BKFR3UN | SEQ ID NO:7 |
| BK2FR3UN | SEQ ID NO:8 |
| $V_λ$ sense primers: | |
| HSCLam1a | SEQ ID NO:9 |
| HSCLam1b | SEQ ID NO:10 |
| HSCLam2 | SEQ ID NO:11 |
| HSCLam3 | SEQ ID NO:12 |
| HSCLam4 | SEQ ID NO:13 |
| HSCLam6 | SEQ ID NO:14 |

-continued

| | |
|---|---|
| HSCLam70 | SEQ ID NO:15 |
| HSCLam78 | SEQ ID NO:16 |
| HSCLam9 | SEQ ID NO:17 |
| $V_\lambda$ antisense primer: | |
| BLFR3UN | SEQ ID NO:18 |
| $V_H$ sense primers: | |
| HFVH1-F | SEQ ID NO:19 |
| HFVH2-F | SEQ ID NO:20 |
| HFVH35-F | SEQ ID NO:21 |
| HFVH4-F | SEQ ID NO:22 |
| $V_H$ antisense primers: | |
| BFR3UN | SEQ ID NO:23 |

Construction of a Chimeric Mouse/Human Fd Fragment by Fusing $V_H$ of LM609 to Human $C_H1$ The phagemid vector pComb3H containing the LM609 Fab sequences was used as a template for amplification of the sequence encoding the N-terminal FR1 through FR3 fragment of LM609's $V_H$ by the PCR primer pair PELSEQ (SEQ ID NO:24)/BFR3UN (SEQ ID NO:25). The sense primer PELSEQ hybridizes to the pe1B leader sequence upstream of the Fd fragment encoding sequence in pComb3H. The antisense primer BFR3UN hybridizes to a sequence that encodes eight C-terminal amino acids of FR3 of $V_H$, which are highly conserved (SEQ ID NO:26), and differ in one amino acid from the corresponding amino acid sequence of LM609's $V_H$ (SEQ ID NO:27).

By overlap extension PCR (See McArn Horton, R., and Readington Pease, L. (1991) RECOMBINATION AND MUTAGENESIS OF DNA SEQUENCES USING PCR IN DIRECTED MUTAGENESIS: A PRACTICAL APPROACH, ed. M. J. McPherson, IRL Press, Oxford, UK, pp. 217–247), the PELSEQ/BFR3UN product was fused to a PCR fragment encoding the HCDR3 (SEQ ID NO:1) of LM609 coupled to FR4 of $V_H$ and the entire $C_H1$ domain of the human anti-gp120 antibody b8. This fragment had been amplified by the PCR primer pair CR501 (SEQ ID NO:28)/CR301 (SEQ ID NO:29). The sense primer CR501 encodes a synthetic link of the nine C-terminal amino acids of FR3, the eight amino acids forming the HCDR3 (SEQ ID NO:1) of LM609, and the six N-terminal amino acids of FR4 of b8. The FR4 of b8 is a preferred choice here because it is identical to FR4 of LM609's $V_H$ with the exception of the C-terminal amino acid, which is A for LM609 and S for b8. The 24-bp overlap of CR501 and BFR3UN allowed to fuse the corresponding PCT products by overlap extension PCR.

The sense primer CR301 hybridizes to a sequence that encodes the C terminus of $C_H1$ and introduces a SpeI site that allows the PCR product to link to the gene III ORF on pComb3H. The product of the overlap extension PCR was cut with XhoI/SpeI, ligated into the appropriately digested phagemid vector pComb3H, and the correct sequence was confirmed by DNA sequencing.

Substitution of the LM609 Light Chain by a Human Light Chain that Contains the LCDR3 of LM609

Using overlap extension PCR, the amplified human sequences encoding the N-terminal FR1 through FR3 fragment of $V_\kappa$ and $V_\lambda$ were fused to PCR fragments encoding the LCDR3 (SEQ ID NO:2) of LM609 coupled to FR4 of human $V_\kappa$ or $V_\lambda$ and the human $C_\kappa$ or $C_\lambda$ domain. Two κ fragments were generated by the PCR primer pairs CR503 (SEQ ID NO:30)/T7B (SEQ ID NO:31) and CR508 (SEQ ID NO:32)/T7B using the sequence of the anti-gp120 antibody b11 in pComb3 as a template.

The sense primers CR503 and CR508 encode a synthetic link of eight C-terminal amino acids of FR3 of human $V_\kappa$ (SEQ ID NO:33 or SEQ ID NO:34), the nine amino acids forming the LCDR3 (SEQ ID NO:2) of LM609, and the seven N-terminal amino acids of FR4 of b11. FR4 of b11 is the preferred choice because it is identical to FR4 of LM609's $V_\kappa$ with the exception of the third N-terminal and C-terminal amino acid, which are G and T in LM609 versus Q and A in b11. The 23-bp overlap of CR503 with BKFR3UN and CR508 with BK2FR3UN allowed to fuse the corresponding PCR products by overlap extension PCR.

The backward primer T7B hybridizes to a pComb3 sequence downstream of the light chain encoding sequence. A λ fragment was generated by the PCR primer pair CR510 (SEQ ID NO:35)/CLext (SEQ ID NO:36) using CLext primed first strand cDNA from human bone marrow as a template.

The sense primer CR510 encodes a synthetic link of seven C-terminal amino acids of FR3 of human $V_\lambda$ (SEQ ID NO:37), the nine amino acids forming the LCDR3 of LM609, and the seven N-terminal amino acids of FR4 of human $V_\lambda$ (SEQ ID NO:38). The 21-bp overlap of CR510 with BLFR3UN allowed to fuse the corresponding PCR products by overlap extension PCR. The backward primer CLext hybridizes to the 3' end of the human $C_\lambda$ encoding sequence and introduces a Xbai site.

The generated light chain encoding sequences were cut with SacI/XbaI and ligated into the appropriately digested phagemid vector pComb3H that contained the chimeric mouse/human Fd fragment. Electrotransformation of the ligation products into *E. coli* strain ER 2537 (New England Biolabs; Beverly, Mass.) resulted in a light chain library consisting of $1.5 \times 10^8$ independent transformants. DNA sequencing revealed the correct assembly of the fused fragments.

Four rounds of panning against immobilized human integrin $\alpha_V\beta_3$ were carried out essentially as described in "High-affinity self-reactive human antibodies by design and selection: targeting the integrin ligand binding site", (*Proc. Natl. Acad. Sci. USA* 90, 10003–10007 (1993)) by C. F. Barbas, III, et al. using 200 ng protein in 25 μl metal buffer (25 mM Tris-HCl, pH 7.5; 137 mM NaCl; 1 mM KCl; 1 mM $MgCl_2$; 1 mM $CaCl_2$; 1 mM $MnCl_2$) for coating, 0.05 percent Tween 20 in TBS for washing, and 10 mg/ml trypsin in TBS for elution. The washing steps were increased from 5 in the first round, to 10 in the second round and 15 in the third and fourth rounds. The output phage pool of each round was monitored by phage ELISA.

After the fourth round phage were produced from single clones and tested for binding to immobilized integrin $\alpha_V\beta_3$ by phage ELISA. Light chain encoding sequences of positive clones were analyzed by DNA sequencing using the primer OMPSEQ (SEQ ID NO:39) that hybridizes to the ompA leader sequence upstream of the light chain encoding sequence in pComb3H.

Substitution of the LM609 Fd Fragment by a Human Fd Fragment that Contains the Heavy Complementarity Determining Region Three (HCDR3) of LM609

Three PCR fragments were fused in one step by overlap extension PCR. Using the selected phagemids from the light chain panning as a template, Fragment 1 was amplified with the PCR primer pair RSC-F (SEQ ID NO:40)/lead-B (SEQ ID NO:41). While the sense primer RSC-F hybridizes to a sequence upstream of the light chain encoding sequence, the antisense primer lead-B hybridizes to a sequence upstream of the Fd fragment encoding sequence. The amplified human sequences encoding the FR1 through FR3 fragment of VH (see above) were used as fragment 2.

Fragment 3 was amplified with the PCR primer pair CR501/HIgG1-B (SEQ ID 42) using the hybrid mouse/human Fd fragment (see above) as a template. The antisense primer HIgG1-B hybridizes to the 3' end of the $C_H1$ encoding sequence. Using the 21-bp overlap of lead-B with the HFVH-F primers and the 24-bp overlap of BFR3UN with CR501, the three fragments were fused and amplified with the PCR primer pair RSC-F/RSC-B (SEQ ID NO:43). The antisense primer RSC-B overlaps with HIgG1-B. RSC-F and RSC-B introduce two asymmetric SfiI sites.

To maintain high complexity, separate PCR reactions were performed for each selected phagemid from the light chain panning (Fragment 1) and for each of the five $V_H$ fragment pools derived from the five first strand cDNA sources (Fragment 2). The generated fragments encoding the selected human light chains linked to human Fd fragments were cut with SfiI and ligated into the appropriately digested phagemid vector pComb3H generating a library of $3 \times 10^7$ independent transformants.

DNA sequencing revealed the correct assembly of the fused DNA fragments. Four rounds of panning against immobilized human integrin $\alpha_V\beta_3$ were carried out exactly as described for the light chain panning. The output phage pool of each round was monitored by phage ELISA. After the fourth round, light chain and Fd fragment encoding sequences were isolated from the selected phagemids by SfiI digestion and subcloned into the compatible expression vector pPhoA-H6HA.

Lysates of individual clones grown in phosphate-deprived medium were analyzed for binding to immobilized integrin $\alpha_V\beta_3$ by ELISA using goat anti-human F(ab')$_2$ conjugated to alkaline phosphatase (Pierce) as secondary antibody. Light chain and Fd fragment encoding sequences of positive clones were analyzed by DNA sequencing using the primers OMPSEQ and PELSEQ, respectively.

Results cDNA Cloning of LM609

Starting from LM609 expressing hybridoma cells, cDNAs encoding λ chain Fd fragments and entire κ chains were cloned by PCR. The PCR products were cloned into the phagemid pComb3H, which is derived from pComb3, and engineered to facilitate the expression of Fab on the surface of M13 filamentous phage. Phage displaying LM609 Fab were selected by panning against integrin $\alpha_V\beta_3$ and the corresponding cDNA sequences were determined. Soluble LM609 Fab purified from *E. coli* was analyzed and found to bind specifically to integrin $\alpha_V\beta_3$ by ELISA.

The approach for the sequential humanization of LM609 by a combination of guided selection and CDR grafting is illustrated in FIG. 1. For the human light chain selection, the mouse Fd fragment is substituted by a chimeric Fd fragment composed of mouse $V_H$ linked to human $C_H1$ to stabilize the hybrid Fab of the first selection step by the interaction of two matching human constant domains, $C_\kappa$ and $C_H1$. A stabilization of the hybrid Fab also stabilizes the antigen binding site.

The guided selection is started by substituting the κ light chain of LM609 with a human κ and λ light chain library that contained the grafted LCDR3 loop of LM609. The corresponding phage libraries displaying hybrid Fab are then selected by four rounds of panning against immobilized integrin $\alpha_V\beta_3$. Though the output number does not increase from round to round, analysis of the output phage pool from each round for binding to integrin $\alpha_V\beta_3$ by phage ELISA reveals an increasing signal. After the fourth round, phage are produced from clones and tested for binding to integrin $\alpha_V\beta_3$ by phage ELISA.

While the majority of these clones give signals that reveal some binding above background, in the present case, six clones gave very strong signals (See FIGS. 3a through 3e). DNA sequence analysis of these clones revealed 3 different light chain sequences. Two light chain sequences found in five out of six positive clones differ only in four amino acids, i.e., are 96 percent identical. The third light chain sequence shares about 80 percent identity with the other two. However, this sequence had two parts, each of which could be aligned to germ-lines of different $V_\kappa$ families, and, thus is deemed likely to have arisen from PCR cross-over, an artifact that has been reported to occur frequently in the amplification antibody sequences.

Referring to FIGS. 3a through 3e, analysis of the six human $V_\kappa$ revealed two groups of highly related κ chain sequences. In addition, the CDR1 loops of all six selected human $V_\kappa$, which are believed to play a role in the assembly of $V_\kappa$ and $V_\lambda$, resemble the corresponding region of LM609 $V_\kappa$. This indicates that the template $V_\lambda$ of LM609 together with the LM609 antigen, the human integrin $\alpha_V\beta_3$, selected for human κ chains that are related to the LM609 κ chain. The fact that no repeated sequences were found may indicate that the grafted LCDR3 loop of LM609, which is identical in all selected human κ chains, is mainly responsible for the contribution of the LM609 κ chain to antigen binding.

This supposition is supported by two additional observations. First, the initial humanization approach was based on the original human κ chain libraries. Four rounds of panning selected a repeated human κ chain with a sequence related to the LM609 κ chain. However, the corresponding hybrid Fab appeared to bind only weakly to human integrin $\alpha_V\beta_3$. Therefore, the LCDR3 loop of LM609 was grafted in the human κ chain libraries, and, though only roughly estimated from ELISA, the binding of the corresponding selected hybrid Fab to human integrin $\alpha_V\beta_3$ improved.

Second, the selected phage were selected by two further rounds of panning against immobilized human integrin $\alpha_V\beta_3$. Again, soluble ones derived from selected phagemids were analyzed for binding to immobilized human integrin $\alpha_V\beta_3$ by ELISA. This time, all of the analyzed 20 clones were found to bind specifically. However, sequencing of 16 clones revealed no repeated sequences. It appears, thus, that a number of different human κ chain sequences that contain the LCDR3 loop of LM609 can substitute the LM609 κ chain without much difference in binding to human integrin $\alpha_V\beta_3$. This finding is believed to be of importance for the therapeutic application of humanized LM609.

Due to allotypic sequence variability, humanized antibodies can be neutralized by the patient's immune system after repeated injections. This problem is avoided by using humanized antibodies with identical antigen binding properties but different amino acid sequences for repeated administrations.

As with the original LM609 light chain, the selected light chains are each κ light chains. Moreover, database screening revealed that they were derived from the same germ-line, namely DPK-26, belonging to the $V_\kappa 6$ family. This speaks in favor of a strong selection towards these sequences because the $V_\kappa 6$ family is not frequently found in human antibodies. An obvious reason for this strong selection is a relatively high sequence similarity of the selected human light chains with the original mouse light chain.

Referring to FIG. 4, for comparison, four clones from the un-selected library were picked randomly and their light chain sequences determined. Three selected human light chains used in the comparison consist of eleven LCDR1 amino acids, the length of the original mouse LCDR1, while only one out of four unselected human light chains shared the same LCDR1 length with the original mouse sequence (see FIG. 4).

Moreover, both LCDR1 and LCDR2 of the selected human light chains are highly similar to the corresponding mouse sequence. The C-terminal amino acid of framework region 2 of the original mouse light chain sequence, a lysine (Lys) shown in brackets in FIG. 4, is an unusual amino acid at this position and, thus may be involved in the formation of the antigen binding site. Interestingly, all the selected human light chain sequences contain a lysine at this position, while all the unselected sequences contain a tyrosine (Tyr) instead. As a matter of fact, the $V_\kappa 6$ family is the only human $V_\kappa$ family that contains a lysine at that position.

Taken together, this evidence shows that the mouse $V_H$ template and the antigen selected for unbiased human $V_\kappa$ sequences are related to the original mouse $V_\kappa$ sequence. Three clones from the light chain selection, revealing weaker binding to integrin $\alpha_V\beta_3$ than the six clones discussed above but still having significant binding above background, were also analyzed by DNA sequencing. These analyses revealed three unrelated $V_\lambda$ sequences, together with selected $V_\kappa$ sequences-except the one that stemmed from the PCR cross-over artefact—were used as templates in the humanization of the heavy chain of LM609.

Based on the aforedescribed humanization strategy, five humanized versions of the anti-human integrin $\alpha_V\beta_3$ monoclonal antibody LM609 were generated. The five version were revealed through the sequence analysis of 14 humanized clones that bind to $\alpha_V\beta_3$. Referring to FIGS. 8a and 8b, the amino acid sequences of a mouse $V_L$ (SEQ ID NO:45) are compared to the amino acid sequences of the version A, and the combined versions (or groups) B, C, D, and E.

Similarly FIGS. 8c through 8e compare the amino acid sequences of a mouse $V_H$ (SEQ ID NO:56) to the amino acid sequences of the five versions (or groups) A–E. Four of these versions, represented by clones 7, 8, and 22 (group B); 4, 31, and 36 (group C); 24, 34, and 40 (group D); and 2 (group E), are highly related in amino acid sequence. The sequence group BCDE in FIGS. 8a and 8b represent the four versions that share an identical $V_L$ domain (SEQ ID NO:49). The amino acid sequence identity of their $V_H$ domains (SEQ ID NOS:50–53), which are all derived from the germ-line DP-65 or the highly related DP-78, is at least 90% for each version.

In contrast, version five includes clones 10, 11, and 37 (A), and represents a humanized version with a $V_H$ domain (SEQ ID NO:54) that is derived from a different germ-line family. This humanized version also contains a different $V_L$ domain (SEQ ID NO:55), which is, however, 95% identical and derived from the same germ-line. Germ-lines were determined by nucleic acid sequence alignment using DNA-PLOT software provided by the VBASE Directory of Human V Gene Sequences from the MRC Centre for Protein Engineering.

By preserving the original complementarity determining region sequences such as the LCDR3 (SEQ ID NO:2) and HCDR3 (SEQ ID NO:1) sequences of LM609, the disclosed humanization strategy ensures epitope conservation. Epitope conservation is a critical demand in the humanization of antibodies, especially in the case of LM609. The function-blocking anti-human integrin $\alpha_V\beta_3$ mouse monoclonal antibody LM609 binds to a yet unidentified nonlinear epitope that involves both the $\alpha_V$ and $\beta_3$ polypeptide chains.

Importantly, by binding to this epitope LM609 induces apoptosis in $\alpha_V\beta_3$ expressing vascular cells, a unique feature among a number of anti-human integrin $\alpha_V\beta_3$ mouse monoclonal antibodies. LM609 does not recognize the related human integrin $\alpha_{IIb}\beta_3$. Any cross-reactivity with human $\alpha_{IIb}\beta_3$, which is expressed on platelets, precludes the use of LM609 as a tool in cancer therapy.

The five humanized versions of LM609, clones 2, 4, 7, 11, and 24, which had been selected by binding to immobilized, thus potentially denatured human integrin $\alpha_V\beta_3$, were tested for binding to native human integrin $\alpha_V\beta_3$ expressed on the cell surface. For this, binding of humanized LM609 to untransfected CS-1 hamster cells and CS-1 hamster cells transfected with either human $\beta_3$ or $\beta_5$ cDNA was analyzed by flow cytometry. Like mouse LM609, but in contrast to a control antibody, all five humanized versions of LM609 revealed specific binding to CS-1 hamster cells transfected with human $\beta_3$ cDNA (See FIGS. 5a–5f).

Figure 6:
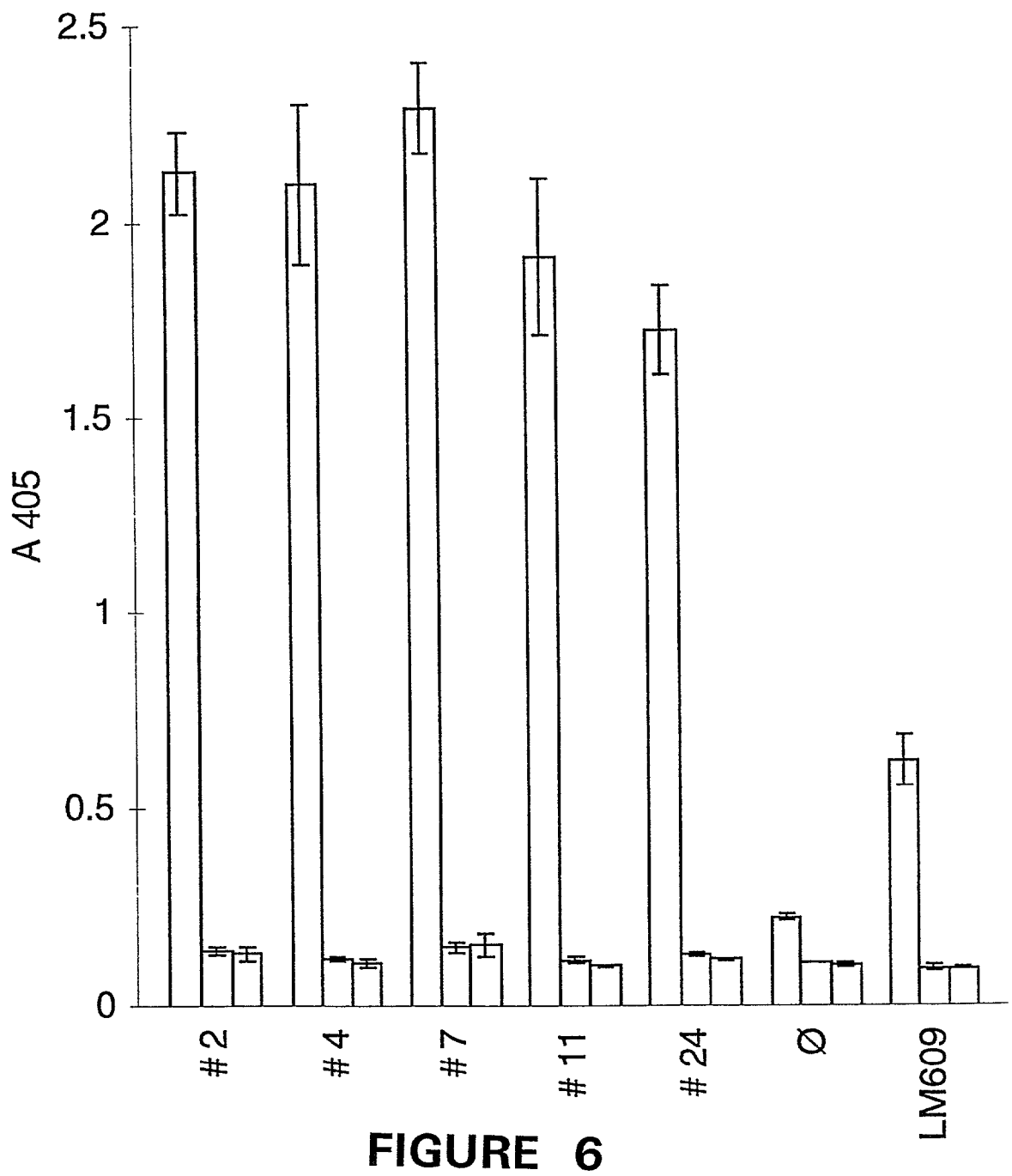
FIG. 6 is a bar graph showing the cross-reactivity of the LM609 antibody, and clones 2, 4, 7, 11, 24, and control antibody, respectively. Columns represent the mean of triplicates, with the left columns indicating binding to human integrin $\alpha_V\beta_3$, the central columns indicating binding to human integrin $\alpha_{IIb}\beta_3$, and the right columns indicating background binding. Error bars indicate standard deviations.

Potential cross-reactivity of humanized LM609 with human integrin $\alpha_{IIb}\beta_3$ was analyzed by ELISA. While antibody Fab-9 with known cross-reactivity bound to both immobilized human integrin $\alpha_V\beta_3$ and $\alpha_{IIb}\beta_3$, cross-reactivity was detected neither for mouse LM609 nor its five humanized versions (See FIG. 6).

Thus, all evidence speaks in favor of epitope conservation through the process of humanization of LM609.

Affinity maturation is a highly relevant step in engineering antibodies for therapeutic applications. By increasing the target affinity, the in vivo concentration of an antibody that must be reached to be effective for therapy is lowered. In addition to reducing the costs of antibody therapy, low effective in vivo concentrations will help to reduce the chance of immune response.

Figure 7:
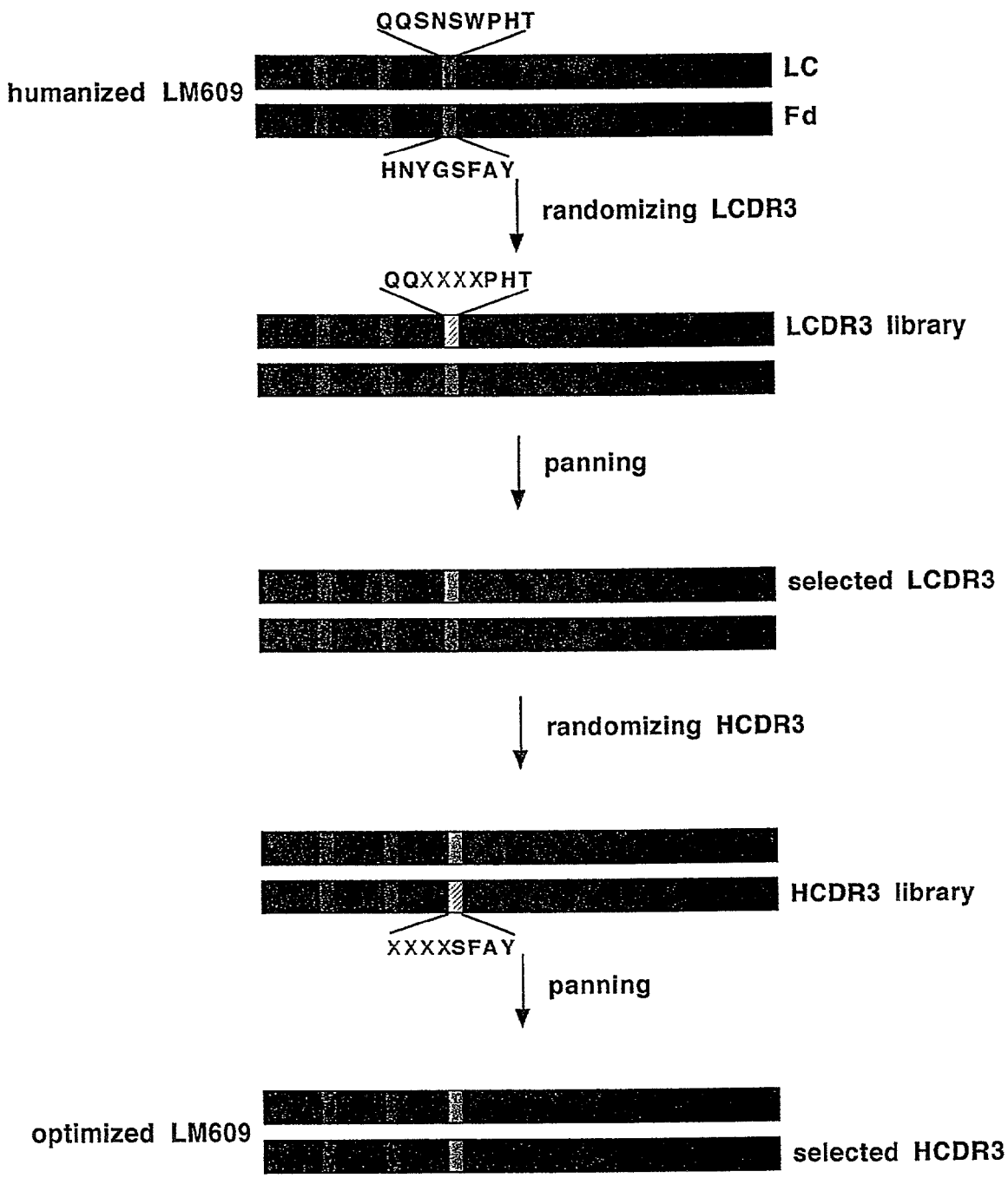
FIG. 7 is a schematic illustration of a stretch of four amino acids in a light chain complementarity determining region three (LCDR3) and a heavy chain complementarity determining region three (HCDR3) being optimized.

The CDR walking strategy for the affinity maturation of antibodies has been described elsewhere, and is known in the relevant art. For the affinity maturation of humanized LM609 a sequential optimization of LCDR3 and HCDR3 was chosen (See FIG. 7). The randomized region in both CDRs was confined to a stretch of four amino acids that revealed highest variability in human antibody sequences. See Kabat, E. A. et al. (1991) SEQUENCES OF PROTEINS OF IMMUNOLOGICAL INTEREST, U.S. Dept of Health and Human Services, Washington, D.C. Using NNK doping (Barbas, C. F. et al., (1994) IN VITRO EVOLUTION OF A NEUTRALIZING HUMAN ANTIBODY TO HIV-1 TO ENHANCE AFFINITY AND BROADEN STRAIN CROSS-REACTIVITY, Proc. Natl. Acad. Sci. USA 91, 3809–3813) the randomization of four codons results in $32^4$ or $1\times10^6$ different nucleotide sequences. Based on this and assuming a Poisson distribution (Clackson, T., and Wells, J. A. (1994) IN VITRO SELECTION FROM PROTEIN AND PEPTIDE LIBRARIES, Trends in Biotechnol. 12, 173–184), $5\times10^6$ independent transformants are required for a complete library with 99 percent confidence. For each of the five humanized versions of LM609 independent LCDR3 randomized libraries were generated. The number of independent transformants in each library lay well above $5\times10^6$ (see Experimental Procedures, below). Ten completely different LCDR3 sequences were obtained when two clones of each of the five libraries were analyzed by DNA sequencing. The three libraries that were based on humanized LM609 clones 2, 4, and 24, which contain identical light chains and highly related heavy chains derived from germ-line DP-65, were pooled. Corresponding to their underlying germ-line sequences the three remaining libraries were named DPK-26ranLCDR3/DP-10, DPK-26ranLCDR3/DP-65, and DPK-26ranLCDR3/DP-78.

These three libraries were selected in parallel.

To improve the selection of higher affinity LCDR3 mutants, a solid phase off-rate selection (Yang, W. P. et al. (1995) CDR WALKING MUTAGENESIS FOR THE AFFINITY MATURATION OF A POTENT HUMAN ANTI-HIV-1 ANTIBODY INTO THE PICOMOLAR RANGE, *J. Mol Biol.* 254, 392–403) was used. In five subsequent cycles of selection 20 μg LM609 IgG was added to the well with 200 or 50 ng immobilized human integrin $\alpha_V\beta_3$ following phage incubation and washing. After 24 hours at room temperature, the well was washed again and bound phage eluted with trypsin. This off-rate selection step is discussed in the following paragraph.

Protein interactions are characterized by thermodynamic and kinetic parameters. While the affinity constant ($K_a = k_{on}/k_{off}$) is an equilibrium constant, the association ($k_{on}$) and dissociation ($k_{off}$) rate constants are more relevant to in vivo processes which are beyond equilibrium. See Williams, A. F. (1991) OUT OF EQUILIBRIUM, *Nature* 352, 473–474. In fact, to occur in vivo, interactions with high affinity, i.e., high $K_a$ values, still rely on rapid association, i.e., high $k_{on}$ values. Antibodies are subject to kinetic selection based on binding target antigens rapidly, in parallel with thermodynamic selection for high affinity binding in order to allow sufficient time for antigen clearance. See Foote, J., and Milstein, C. (1991) KINETIC MATURATION OF AN IMMUNE RESPONSE, *Nature* 352, 530–532. A typical antibody/antigen interaction with a $K_a$ value in the range of $10^9$ M$^{-1}$ associates rapidly with a $k_{on}$ value in the range of $10^5$ to $10^6$ M$^{-1}$s$^{-1}$ and dissociates slowly with a $k_{off}$ value in the range of $10^{-3}$ to $10^{-4}$ s$^{-1}$. An off-rate selection for affinity maturation, i.e., decreasing $k_{off}$, requires consideration of the half-life of the antibody/antigen interactions that is given by $t_{1/2} = \ln 2/k_{off}$. An antibody/antigen interaction with $k_{off} = 1 \times 10^{-4}$ s$^{-1}$ has a half-life of about 2 hours. A tenfold lower dissociation constant, i.e., $k_{off} = 1 \times 10^{-5}$ s$^{-1}$, results in a tenfold longer half-life, i.e., about 20 hours. These long half-lives limit the off-rate selection in our affinity maturation protocol. Using a reasonable time frame, antibodies with dissociation constants below $1 \times 10^{-6}$ s$^{-1}$ can not be enriched even after multiple selection cycles. However, using a similar protocol, an antibody was selected against gp120 with a $k_{off}$ value in the range of $10^{-6}$ s$^{-1}$. The corresponding affinity constant was in the range of $10^{11}$ M$^{-1}$, a more than 400-fold improvement of the parental antibody.

Eight clones from each of the three independently selected libraries were analyzed by DNA sequencing. The LCDR3 sequences are shown in Table 1, below.

TABLE 1

Selected LCDR3 Mutants

| Kabat position[1] | 91 | 92 | 93 | 94 |
|---|---|---|---|---|
| LM609 | Ser | Asn | Ser | Trp |
| Library DPK-26ranLCDR3/DP-10[2] | Ser | Gln | Trp | Trp |
| | Ser | Gln | Trp | Trp |
| | Ser | Gln | Trp | Trp |
| | Ser | Gln | Val | Trp |
| | Ser | Gln | Phe | Trp |
| | Ser | Gln | Phe | His |
| | Ser | Gln | Phe | His |
| Library DPK-26ranLCDR3/DP-65[3] | Ser | Gln | Phe | Trp |
| | Ser | Gln | Phe | Trp |
| | Ser | Gln | Phe | Trp |
| | Ser | Gln | Phe | Trp |
| | Ser | Gln | Phe | Trp |
| | Ser | Gln | Phe | Trp |
| | Ser | Gln | Phe | Trp |
| | Ser | Gln | Phe | Trp |
| Library DPK-26ranLCDR3/DP-78[4] | Ser | Gln | Trp | Trp |
| | Ser | Gln | Trp | Trp |
| | Ser | Gln | Val | Trp |
| | Ser | Gln | Val | Trp |
| | Ser | Gln | Phe | Trp |
| | Ser | Gln | Phe | Trp |
| | Ser | Gln | Tyr | Trp |
| | Ser | Gln | His | Trp |

[1] cf. Kabat, et al. (1991)
[2] based on humanized LM609 clone 11
[3] based on humanized LM609 clones 2, 4, and 24
[4] based on humanized LM609 clone 7

A strong selection towards a consensus sequence that is highly related to the original sequence took place. All 24 analyzed clones contain a serine (Ser) in Position 91 and a glutamine (Gln) in Position 92 of the randomized region. The corresponding amino acids in the parental LCDR3 are serine (Ser) and asparagine (Asn), respectively. Interestingly, all three serine codons of the NNK genetic code (TCT, TCG, and ACT) are found in Position 91. Position 94, a tryptophane (Trp) in the parental LCDR3, was re-selected in 22 out of 24 clones. Two clones contain a histidine (His) instead. Only Position 93 reveals greater diversity. The original serine (Ser) is substituted by an aromatic or hydrophobic amino acid, either phenylalanine (Phe-13/24), tryptophane (Trp-6/24), valine (Val-3/24), tyrosine (Tyr-1/24) or histidine (His-1/24). Analysis of the heavy chain sequences revealed that no cross-contamination between the three independently selected libraries took place. All eight clones selected from library DPK-26ranLCDR3/DP-65, which contained the pool of the three highly related heavy chains encoding sequences derived from germ-line DP-65, were identical and derived from humanized LM609 clone 24.

The conserved LCDR3 sequence speaks in favor of a highly defined epitope on human integrin $\alpha_V\beta_3$. Though binding to native human integrin $\alpha_V\beta_3$ on the cell surface needs to be proved yet, an epitope shift towards denatured human integrin $\alpha_V\beta_3$ is unlikely. The selected phage pools were analyzed for binding to human integrin $\alpha_V\beta_3$ by phage ELISA and in competition with LM609 IgG. These analyses suggest a significantly lower dissociation constant of the selected clones in comparison with LM609 as well as humanized LM609. The substitution of the original serine in Position 3 by an aromatic residue may give rise to a new hydrophobic interaction with a strong impact on the overall affinity.

Experimental Procedures

Materials

LM609 IgG purified from hybridoma cultures was provided by Dr. David A. Cheresh. Human integrin $\alpha_V\beta_3$ and human integrin $\alpha_{IIb}\beta_3$ were from sources described in HIGH-AFFINITY SELF-REACTIVE HUMAN ANTIBODIES BY DESIGN AND SELECTION: TARGETING THE INTEGRIN LIGAND BINDING SITE, Barbas III, C. F., et al. (1993) *Proc. Natl. Acad. Sci. USA*, 90, 10003–10007. Untransfected CS-1 hamster cells and CS-1 hamster cells transfected with either human $\beta_3$ or $\beta_5$ cDNA were obtained from Dr. David A. Cheresh (Filardo, E. J., et al. (1995) REQUIREMENT OF THE NPXY MOTIF IN THE INTEGRIN $\beta_3$ SUBUNIT CYTOPLASMIC TAIL FOR MELANOMA CELL MIGRATION IN VITRO AND IN VIVO, *J. Cell Biol.* 130, 441–450) and maintained in RPMI medium supplemented with 5% fetal calf serum (FCS) at 37° C. in 7% $CO_2$.

*E. Coli* Expression of Soluble Humanized LM609 Fab

Following phage library panning, the SfiI insert of the selected humanized LM609 phagemid pool was cloned into the *E. coli* expression vector pPhoA-H6HA (See Rader, C., and Barbas III, C. F. (1997) PHAGE DISPLAY OF COMBINATORIAL ANTIBODY LIBRARIES, *Curr. Opin. Biotechnol.* 8, 503–508) for detection of $\alpha_V\beta_3$ binders. Sequence determination of 14 clones revealed five different humanized LM609 versions, represented by clones 2, 4, 7, 11, and 24. cDNAs of these clones were cut out by SacI/SpeI digestion and ligated into SacI/NheI cut pComb3H, thereby removing the gene III fragment encoding cDNA of pComb3H and allowing for production of soluble Fab (See Rader, C. (1997) *Curr. Opin. Biotechnol.* 8, 503–508). The ligation products were electrotrasformed into *E. coli* strain XL1-Blue. Fab production was induced by addition of isopropyl β-D-thiogalactopyranoside as described (Barbas III, C. F., et al. (1991) ASSEMBLY OF COMBINATORIAL ANTIBODY LIBRARIES ON PHAGE SURFACES: THE GENE III SITE, *Proc. Natl. Acad. Sci. USA* 88, 7978–7982).

ELISA

Human integrins $\alpha_V\beta_3$ and $\alpha_{IIb}\beta_3$ were coated for 90 minutes at 37° C. on a 96-well plate (Costar #3690) at a concentration of 60 ng/25 µl metal buffer (25 mM Tris-HCl, pH 7.5; 137 mM NaCl; 1 mM KCl; 1 mM $MgCl_2$; 1 mM $CaCl_2$; 1 mM $MnCl_2$) per well. Following blocking with 150 µl 3% BSA/TBS for 1 hour at 37° C., 25 µl crude supernatants from overnight cultures of *E. coli* strain XL1-Blue expressing soluble LM609 or humanized LM609 Fab were added to the well and incubated for 2 hours at 37° C. Binding of each of the supernatants to wells coated with human integrin $\alpha_V\beta_3$ and $\alpha_{IIb}\beta_3$ as well as to uncoated but blocked wells was analyzed in triplicates. As a positive control, 25 µl of 50 ng/µl purified Fab-9, an antibody binding to both human integrin $\alpha_V\beta_3$ and $\alpha_{IIb}\beta_3$ (Barbas III, et al. (1993) *Proc. Natl. Acad. Sci. USA* 90, 10003–10007), and as a negative control, 25 µl of plain bacterial culture medium were used. After extensive washing with tap water, 25 µl of a 1:2,000 dilution of goat anti-mouse F(ab')$_2$ or goat anti-human F(ab')$_2$ conjugated with alkaline phosphatase (Pierce #31324 or 31312, respectively) in 1% BSA/TBS was added to the well and incubated for 1 hour at 37° C. Following another extensive washing with tap water, 50 µl of alkaline phosphatase substrate (5 mg disodium p-nitrophenyl phosphate hexahydrate (Sigma #104–105) dissolved in 5 ml 10% diethanolamine, 1 mM $MgCl_2$, 3 mM $NaN_3$, pH 9.8) were added to the well. The plate was analyzed with an ELISA reader (Molecular Devices) after 15 minutes incubation at room temperature.

Flow Cytometry

Flow cytometry was performed using a Becton Dickinson FACScan instrument. For each determination, $5 \times 10^3$ untransfected hamster CS-1 cells or hamster CS-1 cells expressing either human $\beta_3$ or $\beta_5$, were analyzed. Indirect immunofluorescence staining was achieved with crude lysates of *E. coli* strain XL1-Blue expressing soluble humanized LM609 Fab or, as a negative control, an unrelated human Fab. A 1:100 dilution of FITC-conjugated goat anti-human F(ab')$_2$ (Jackson #109-096-097) was used for detection.

Construction of LCDR3 Libraries

Humanized LM609 clones 2, 4, 7, 11, and 24 in pPhoA-H6HA were separately utilized as templates for overlap extension PCR mutagenesis as described (Barbas III, et al. (1994) IN VITRO EVOLUTION OF A NEUTRALIZING HUMAN ANTIBODY TO HIV-1 TO ENHANCE AFFINITY AND BROADEN STRAIN CROSS-REACTIVITY, *Proc. Natl. Acad. Sci. USA* 91, 3809–3813). The two fragments required for this procedure were obtained with the PCR primer pairs OMPSEQ (SEQ ID NO:39)/CR320 (SEQ ID NO:46) and CR520 (SEQ ID NO:47)/DPSEQ (SEQ ID NO:48), respectively. The resulting five cDNAs with randomized LCDR3 were cut with SfiI, ligated into the appropriately digested phagemid vector pComb3H, and electrotransformed into *E. coli* strain ER 2537. Two clones of each of the five libraries were analyzed by DNA sequencing and revealed correct assembly as well as 10 different LCDR3 sequences. Prior to selection, libraries based on clones 2, 4, and 24 ($V_L$ germ-line DP-26; $V_H$ germ-line DP-65) were combined to give a complexity of $6 \times 10^7$ independent transformants. Libraries based on clone 11 ($V_L$ germ-line DP-26; $V_H$ germ-line DP-10) and 7 ($V_L$ germ-line DP-26; $V_H$ germ-line DP-78) were kept separate with a complexity of $3 \times 10^7$ and $4 \times 10^7$ independent transformants, respectively.

Selection of LCDR3 Libraries

The three LCDR3 libraries were separately selected by panning against immobilized integrin $\alpha_V\beta_3$ for six cycles. Panning was performed substantially as described hereinabove for the LM609 humanization. The concentration of human integrin $\alpha_V\beta_3$ for coating was 200 ng/25 µl in the first through fourth cycles and 50 ng/25 µl in the fifth and sixth cycles. Also, the input number of phage, in the range of $10^{12}$ in the first through fourth cycles as usual, was decreased by a factor of 10 in the fifth cycle and by a factor of 100 in the sixth cycle. In the second through the sixth cycles of selection 20 µg LM609 IgG in 50 µl metal buffer (25 mM Tris-HCl, pH 7.5; 137 mM NaCl; 1 mM KCl; 1 mM $MgCl_2$; 1 mM $CaCl_2$; 1 mM $MnCl_2$) was added to the well following removal of unbound phage by five to ten washing steps. The plate was then incubated for 24 hours at room temperature (off-rate selection) prior to five additional washing steps and trypsin elution as described. After the sixth cycle phage were produced from single clones and tested for binding to immobilized human integrin $\alpha_V\beta_3$ by phage ELISA using a sheep anti-M13 antibody conjugated with horseradish peroxidase (Pharmacia #27-9411-01) as a secondary antibody. Light chain and heavy chain encoding sequences of positive clones were analyzed by DNA sequencing using the primers OMPSEQ (SEQ ID NO:39) and PELSEQ (SEQ ID NO:24), respectively.

Optimization of LM609 by CDR Randomization

In addition to the humanization, LM609 can be optimized in two respects: First, by increasing the affinity to $\alpha_V\beta_3$ and, second, by broadening the species cross-reactivity. Increased affinity of engineered LM609 increases the potency and decreases the cost of a potential cancer therapy.

The original mouse monoclonal antibody LM609 already has a broad species cross-reactivity. It binds to human, dog, cat, bovine, rabbit, and chick but not mouse $\alpha_V\beta_3$. The fact that LM609 does not recognize host $\alpha_V\beta_3$ in the mouse models of human cancer is a major concern for the therapeutic applicability of LM609. Engineered LM609 binding to both human and mouse $\alpha_V\beta_3$ would be an important tool towards clinical trials. In vitro methods for the improvement of monoclonal antibody affinity include chain shuffling (See Marks, J. D., et al. (1992) BY-PASSING IMMUNIZATION: BUILDING HIGH HUMAN ANTIBODIES BY CHAIN SHUFFLING, *Bio/Technology* 10, 779–783). Binding to α$_v$β$_3$ can be further improved by subsequent CDR randomization, an approach termed CDR walking (See Barbas III, C. F., et al. (1994) IN VITRO EVOLUTION OF A NEUTRALIZING HUMAN ANTIBODY TO HIV-1 TO ENHANCE AFFINITY AND BROADEN STRAIN CROSS-REACTIVITY, *Proc. Natl. Acad. Sci. USA* 91, 3809–3813). The in vitro strategies for humanization and affinity improvement of LM609 are likely to generate cross-reactivity with mouse α$_v$β$_3$ concurrently.

Directed selection for mouse α$_v$β$_3$ recognition is complicated by the fact that mouse α$_v$β$_3$ has not been purified yet. However, several mouse cell lines, e.g., NIH/3T3, are known to express α$_v$β$_3$ and, thus, may be included in the screening procedure.

The foregoing discussion and the accompanying examples are presented as illustrative, and are not to be taken as limiting. Still other variations within the spirit and scope of this invention are possible and will readily present themselves to those skilled in the art.

SEQUENCE LISTING

```
<160> NUMBER OF SEQ ID NOS: 56

<210> SEQ ID NO 1
<211> LENGTH: 8
<212> TYPE: PRT
<213> ORGANISM: Mus Musculus
<220> FEATURE:

<400> SEQUENCE: 1

His Asn Tyr Gly Ser Phe Ala Tyr
 1               5

<210> SEQ ID NO 2
<211> LENGTH: 9
<212> TYPE: PRT
<213> ORGANISM: Mus Musculus
<220> FEATURE:

<400> SEQUENCE: 2

Gln Gln Ser Asn Ser Trp Pro His Thr
 1               5

<210> SEQ ID NO 3
<211> LENGTH: 37
<212> TYPE: DNA
<213> ORGANISM: Homo Sapiens

<400> SEQUENCE: 3
gggcccaggc ggccgagctc cagatgaccc agtctcc                              37

<210> SEQ ID NO 4
<211> LENGTH: 37
<212> TYPE: DNA
<213> ORGANISM: Homo Sapiens
<220> FEATURE:

<400> SEQUENCE: 4
gggcccaggc ggccgagctc gtgatgacyc agtctcc                              37

<210> SEQ ID NO 5
<211> LENGTH: 37
<212> TYPE: DNA
<213> ORGANISM: Homo Sapiens
<220> FEATURE:

<400> SEQUENCE: 5
gggcccaggc ggccgagctc gtgwtgacrc agtctcc                              37

<210> SEQ ID NO 6
<211> LENGTH: 37
<212> TYPE: DNA
<213> ORGANISM: Homo Sapiens
```

```
<220> FEATURE:

<400> SEQUENCE: 6
gggcccaggc ggccgagctc acactcacgc agtctcc                            37

<210> SEQ ID NO 7
<211> LENGTH: 23
<212> TYPE: DNA
<213> ORGANISM: Homo Sapiens
<220> FEATURE:

<400> SEQUENCE: 7
cagtaataca ctgcaaaatc ttc                                           23

<210> SEQ ID NO 8
<211> LENGTH: 23
<212> TYPE: DNA
<213> ORGANISM: Homo Sapiens
<220> FEATURE:

<400> SEQUENCE: 8
cagtaataaa ccccaacatc ctc                                           23

<210> SEQ ID NO 9
<211> LENGTH: 40
<212> TYPE: DNA
<213> ORGANISM: Homo Sapiens
<220> FEATURE:

<400> SEQUENCE: 9
gggcccaggc ggccgagctc gtgbtgacgc agccgccctc                         40

<210> SEQ ID NO 10
<211> LENGTH: 40
<212> TYPE: DNA
<213> ORGANISM: Homo Sapiens
<220> FEATURE:

<400> SEQUENCE: 10
gggcccaggc ggccgagctc gtgctgactc agccaccctc                         40

<210> SEQ ID NO 11
<211> LENGTH: 43
<212> TYPE: DNA
<213> ORGANISM: Homo Sapiens
<220> FEATURE:

<400> SEQUENCE: 11
gggcccaggc ggccgagctc gccctgactc agcctccctc cgt                     43

<210> SEQ ID NO 12
<211> LENGTH: 46
<212> TYPE: DNA
<213> ORGANISM: Homo Sapiens
<220> FEATURE:

<400> SEQUENCE: 12
gggcccaggc ggccgagctc gagctgactc agccaccctc agtgtc                  46

<210> SEQ ID NO 13
<211> LENGTH: 40
<212> TYPE: DNA
<213> ORGANISM: Homo Sapiens
<220> FEATURE:
```

```
<400> SEQUENCE: 13
gggcccaggc ggccgagctc gtgctgactc aatcgccctc                    40

<210> SEQ ID NO 14
<211> LENGTH: 40
<212> TYPE: DNA
<213> ORGANISM: Homo Sapiens
<220> FEATURE:

<400> SEQUENCE: 14
gggcccaggc ggccgagctc atgctgactc agccccactc                    40

<210> SEQ ID NO 15
<211> LENGTH: 40
<212> TYPE: DNA
<213> ORGANISM: Homo Sapiens
<220> FEATURE:

<400> SEQUENCE: 15
gggcccaggc ggccgagctc gggcagactc agcagctctc                    40

<210> SEQ ID NO 16
<211> LENGTH: 40
<212> TYPE: DNA
<213> ORGANISM: Homo Sapiens
<220> FEATURE:

<400> SEQUENCE: 16
gggcccaggc ggccgagctc gtggtgacyc aggagccmtc                    40

<210> SEQ ID NO 17
<211> LENGTH: 40
<212> TYPE: DNA
<213> ORGANISM: Homo Sapiens
<220> FEATURE:

<400> SEQUENCE: 17
gggcccaggc ggccgagctc gtgctgactc agccaccttc                    40

<210> SEQ ID NO 18
<211> LENGTH: 21
<212> TYPE: DNA
<213> ORGANISM: Homo Sapiens
<220> FEATURE:

<400> SEQUENCE: 18
gcagtaataa tcagcctcrt c                                        21

<210> SEQ ID NO 19
<211> LENGTH: 44
<212> TYPE: DNA
<213> ORGANISM: Homo Sapiens
<220> FEATURE:

<400> SEQUENCE: 19
gctgcccaac cagccatggc ccaggtgcag ctggtgcagt ctgg               44

<210> SEQ ID NO 20
<211> LENGTH: 44
<212> TYPE: DNA
<213> ORGANISM: Homo Sapiens
<220> FEATURE:

<400> SEQUENCE: 20
```
gctgcccaac cagccatggc ccagatcacc ttgaaggagt ctgg                    44

<210> SEQ ID NO 21
<211> LENGTH: 44
<212> TYPE: DNA
<213> ORGANISM: Homo Sapiens
<220> FEATURE:

<400> SEQUENCE: 21
gctgcccaac cagccatggc cgaggtgcag ctggtgsagt ctgg                    44

<210> SEQ ID NO 22
<211> LENGTH: 44
<212> TYPE: DNA
<213> ORGANISM: Homo Sapiens
<220> FEATURE:

<400> SEQUENCE: 22
gctgcccaac cagccatggc ccaggtgcag ctgcaggagt cggg                    44

<210> SEQ ID NO 23
<211> LENGTH: 24
<212> TYPE: DNA
<213> ORGANISM: Homo Sapiens
<220> FEATURE:

<400> SEQUENCE: 23
cgcacagtaa tacacggccg tgtc                                         24

<210> SEQ ID NO 24
<211> LENGTH: 21
<212> TYPE: DNA
<213> ORGANISM: Artificial Sequence
<220> FEATURE:
<223> OTHER INFORMATION: PCR Primer for PelB Leader Sequence

<400> SEQUENCE: 24
acctattgcc tacggcagcc g                                            21

<210> SEQ ID NO 25
<211> LENGTH: 24
<212> TYPE: DNA
<213> ORGANISM: Homo Sapiens
<220> FEATURE:

<400> SEQUENCE: 25
cgcacagtaa tacacggccg tgtc                                         24

<210> SEQ ID NO 26
<211> LENGTH: 8
<212> TYPE: PRT
<213> ORGANISM: Homo Sapiens
<220> FEATURE:

<400> SEQUENCE: 26

Asp Thr Ala Val Tyr Tyr Cys Ala
 1               5

<210> SEQ ID NO 27
<211> LENGTH: 8
<212> TYPE: PRT
<213> ORGANISM: Mus Musculus
<220> FEATURE:

<400> SEQUENCE: 27

```
Asp Thr Ala Met Tyr Tyr Cys Ala
 1               5
```

<210> SEQ ID NO 28
<211> LENGTH: 69
<212> TYPE: DNA
<213> ORGANISM: Artificial Sequence
<220> FEATURE:
<223> OTHER INFORMATION: Synthetic PCR Primer

<400> SEQUENCE: 28

| | |
|---|---:|
| gacacggccg tgtattactg tgcgcgtcat aactacggca gttttgctta ctggggccag | 60 |
| ggaaccctg | 69 |

<210> SEQ ID NO 29
<211> LENGTH: 42
<212> TYPE: DNA
<213> ORGANISM: Artificial Sequence
<220> FEATURE:
<223> OTHER INFORMATION: Synthetic PCR Primer

<400> SEQUENCE: 29

| | |
|---|---:|
| gaggaggagg aggagactag ttttgtcaca agatttgggc tc | 42 |

<210> SEQ ID NO 30
<211> LENGTH: 73
<212> TYPE: DNA
<213> ORGANISM: Artificial Sequence
<220> FEATURE:
<223> OTHER INFORMATION: Synthetic PCR Primer

<400> SEQUENCE: 30

| | |
|---|---:|
| gaagattttg cagtgtatta ctgcccaaca gagtaacagc tggcctcaca cgtttggcca | 60 |
| ggggaccaag ctg | 73 |

<210> SEQ ID NO 31
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 31

| | |
|---|---:|
| aatacgactc actatagggc g | 21 |

<210> SEQ ID NO 32
<211> LENGTH: 72
<212> TYPE: DNA
<213> ORGANISM: Artificial Sequence
<220> FEATURE:
<223> OTHER INFORMATION: Synthetic PCR Primer

<400> SEQUENCE: 32

| | |
|---|---:|
| gaggatgttg gggtttatta ctgccaacag agtaacagct ggcctcacac gtttggccag | 60 |
| gggaccaagc tg | 72 |

<210> SEQ ID NO 33
<211> LENGTH: 8
<212> TYPE: PRT
<213> ORGANISM: Homo Sapiens
<220> FEATURE:

<400> SEQUENCE: 33

Glu Asp Phe Ala Val Tyr Tyr Cys

<210> SEQ ID NO 34
<211> LENGTH: 8
<212> TYPE: PRT
<213> ORGANISM: Homo Sapiens
<220> FEATURE:

<400> SEQUENCE: 34

Glu Asp Val Gly Val Tyr Tyr Cys
 1               5

<210> SEQ ID NO 35
<211> LENGTH: 69
<212> TYPE: DNA
<213> ORGANISM: Artificial Sequence
<220> FEATURE:
<223> OTHER INFORMATION: Synthetic PCR Primer

<400> SEQUENCE: 35
gaygaggctg attattactg ccaacagagt aacagctggc ctcacacgtt cggcggaggg     60
accaagctg                                                            69

<210> SEQ ID NO 36
<211> LENGTH: 50
<212> TYPE: DNA
<213> ORGANISM: Artificial Sequence
<220> FEATURE:
<223> OTHER INFORMATION: Synthetic PCR Primer

<400> SEQUENCE: 36
agagagagag agagagagag cgccgtctag aattatgaac attctgtagg                50

<210> SEQ ID NO 37
<211> LENGTH: 7
<212> TYPE: PRT
<213> ORGANISM: Homo Sapiens

<400> SEQUENCE: 37

Asp Glu Ala Asp Tyr Tyr Cys
 1               5

<210> SEQ ID NO 38
<211> LENGTH: 7
<212> TYPE: PRT
<213> ORGANISM: Homo Sapiens
<220> FEATURE:

<400> SEQUENCE: 38

Phe Gly Gly Gly Thr Lys Leu
 1               5

<210> SEQ ID NO 39
<211> LENGTH: 22
<212> TYPE: DNA
<213> ORGANISM: Artificial Sequence
<220> FEATURE:
<223> OTHER INFORMATION: Synthetic PCR Primer

<400> SEQUENCE: 39
aagacagcta tcgcgattgc ag                                              22

<210> SEQ ID NO 40
<211> LENGTH: 41
<212> TYPE: DNA

<213> ORGANISM: Artificial Sequence
<220> FEATURE:
<223> OTHER INFORMATION: Synthetic PCR Primer

<400> SEQUENCE: 40
gaggaggagg aggaggaggc ggggcccagg cggccgagct c        41

<210> SEQ ID NO 41
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 41
ggccatggct ggttgggcag c        21

<210> SEQ ID NO 42
<211> LENGTH: 42
<212> TYPE: DNA
<213> ORGANISM: Artificial Sequence
<220> FEATURE:
<223> OTHER INFORMATION: Synthetic PCR Primer

<400> SEQUENCE: 42
gcagagccca atcttgtga cactagtggc caggccggcc ag        42

<210> SEQ ID NO 43
<211> LENGTH: 41
<212> TYPE: DNA
<213> ORGANISM: Artificial Sequence
<220> FEATURE:
<223> OTHER INFORMATION: Synthetic PCR Primer

<400> SEQUENCE: 43
gaggaggagg aggaggagcc tggccggcct ggccactagt g        41

<210> SEQ ID NO 44
<211> LENGTH: 130
<212> TYPE: PRT
<213> ORGANISM: Mus Musculus
<220> FEATURE:

<400> SEQUENCE: 44

Leu Glu Glu Ser Gly Gly Gly Leu Val Lys Pro Gly Ser Leu Lys
 1               5                  10                  15

Leu Ser Cys Ala Ala Ser Gly Phe Ala Phe Ser Ser Tyr Asp Met Ser
                 20                  25                  30

Trp Val Arg Gln Ile Pro Glu Lys Arg Leu Glu Trp Val Ala Lys Val
             35                  40                  45

Ser Gly Gly Gly Ser Thr Tyr Tyr Leu Asp Thr Val Gln Gly Arg
     50                  55                  60

Phe Thr Ile Ser Arg Asp Asn Ala Lys Asn Thr Leu Tyr Leu Gln Met
65                  70                  75                  80

Ser Ser Leu Asn Ser Glu Asp Thr Ala Met Tyr Tyr Cys Ala Arg His
                 85                  90                  95

Asn Tyr Gly Ser Phe Ala Tyr Trp Gly Gln Gly Thr Leu Val Thr Val
            100                 105                 110

Ser Ala Ala Lys Thr Thr Pro Pro Ser Val Tyr Pro Leu Ala Pro Gly
        115                 120                 125

Ser Ala
    130

<210> SEQ ID NO 45
<211> LENGTH: 109
<212> TYPE: PRT
<213> ORGANISM: Mus Musculus
<220> FEATURE:

<400> SEQUENCE: 45

Glu Leu Val Met Thr Gln Thr Pro Ala Thr Leu Ser Val Thr Pro Gly
 1               5                  10                  15

Asp Ser Val Ser Leu Ser Cys Arg Ala Ser Gln Ser Ile Ser Asn His
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro His
                85                  90                  95

Thr Phe Gly Gly Gly Thr Lys Leu Glu Ile Lys Arg Ala
            100                 105

<210> SEQ ID NO 46
<211> LENGTH: 57
<212> TYPE: DNA
<213> ORGANISM: Artificial Sequence
<220> FEATURE:
<221> NAME/KEY: misc_feature
<222> LOCATION: (1)...(57)
<223> OTHER INFORMATION: n = A,T,C or G
<220> FEATURE:
<223> OTHER INFORMATION: Synthetic PCR Primer

<400> SEQUENCE: 46
ggtcccctgg ccaaacgtgt gaggmnnmnn mnnmnnctgt tggcagtaat acactgc        57

<210> SEQ ID NO 47
<211> LENGTH: 23
<212> TYPE: DNA
<213> ORGANISM: Artificial Sequence
<220> FEATURE:
<223> OTHER INFORMATION: Synthetic PCR Primer

<400> SEQUENCE: 47
cctcaccgtt tggccagggg acc                                             23

<210> SEQ ID NO 48
<211> LENGTH: 21
<212> TYPE: DNA
<213> ORGANISM: Artificial Sequence
<220> FEATURE:
<223> OTHER INFORMATION: Synthetic PCR Primer

<400> SEQUENCE: 48
agaagcgtag tccggaacgt c                                               21

<210> SEQ ID NO 49
<211> LENGTH: 109
<212> TYPE: PRT
<213> ORGANISM: Artificial Sequence
<220> FEATURE:
<223> OTHER INFORMATION: Hybrid mouse - human sequence

<400> SEQUENCE: 49

Glu Leu Val Met Thr Gln Ser Pro Glu Phe Gln Ser Val Thr Pro Lys
1               5                   10                  15

Glu Thr Val Thr Ile Thr Cys Arg Ala Ser Gln Asp Ile Gly Thr Ser
                20                  25                  30

Leu His Trp Tyr Gln Gln Lys Pro Gly Gln Ser Pro Lys Leu Leu Ile
            35                  40                  45

Lys Tyr Ala Ser Gln Pro Val Phe Gly Val Pro Ser Arg Phe Arg Gly
        50                  55                  60

Ser Gly Ser Gly Thr Asp Phe Thr Leu Thr Ile Tyr Ser Leu Glu Ala
65                  70                  75                  80

Glu Asp Phe Ala Val Tyr Tyr Cys Gln Gln Ser Asn Ser Trp Pro His
                85                  90                  95

Thr Phe Gly Gln Gly Thr Lys Leu Glu Ile Lys Arg Thr
                100                 105

<210> SEQ ID NO 50
<211> LENGTH: 118
<212> TYPE: PRT
<213> ORGANISM: Artificial Sequence
<220> FEATURE:
<223> OTHER INFORMATION: Hybrid mouse - human sequence

<400> SEQUENCE: 50

Gln Val Gln Leu Gln Glu Ser Gly Pro Gly Leu Val Lys Pro Ser Gln
1               5                   10                  15

Thr Leu Ser Leu Thr Cys Thr Val Ser Gly Ala Ser Ile Ser Arg Gly
                20                  25                  30

Gly Tyr Tyr Trp Ser Trp Ile Arg Gln Tyr Pro Gly Lys Gly Leu Glu
            35                  40                  45

Trp Ile Gly Tyr Ile His His Ser Gly Ser Thr Tyr Tyr Asn Pro Ser
        50                  55                  60

Leu Lys Ser Arg Val Thr Ile Ala Ile Asp Thr Ser Lys Asn Gln Leu
65                  70                  75                  80

Ser Leu Arg Leu Thr Ser Val Thr Ala Ala Asp Thr Ala Val Tyr Tyr
                85                  90                  95

Cys Ala Arg His Asn Tyr Gly Ser Phe Ala Tyr Trp Gly Gln Gly Thr
                100                 105                 110

Leu Val Thr Val Ser Ser
        115

<210> SEQ ID NO 51
<211> LENGTH: 118
<212> TYPE: PRT
<213> ORGANISM: Artificial Sequence
<220> FEATURE:
<223> OTHER INFORMATION: Hybrid mouse - human sequence

<400> SEQUENCE: 51

Gln Val Gln Leu Gln Glu Ser Gly Pro Gly Leu Val Lys Pro Ser Gln
1               5                   10                  15

Thr Leu Phe Leu Thr Cys Thr Val Ser Gly Gly Ser Ile Ser Ser Gly
                20                  25                  30

Gly Tyr Tyr Trp Ser Trp Ile Arg His Pro Gly Lys Gly Leu Glu
            35                  40                  45

Trp Ile Gly Tyr Ile His His Arg Ala Ala Pro Tyr Tyr Asn Pro Ser
        50                  55                  60

```
Leu Lys Ser Arg Val Thr Ile Ser Val Asp Thr Ser Arg Asn Gln Ile
 65                  70                  75                  80

Ser Leu Lys Leu Arg Ser Val Thr Ala Ala Asp Thr Ala Val Tyr Tyr
                 85                  90                  95

Cys Ala Arg His Asn Tyr Gly Ser Phe Ala Tyr Trp Gly Gln Gly Thr
                100                 105                 110

Leu Val Thr Val Ser Ser
        115
```

<210> SEQ ID NO 52
<211> LENGTH: 118
<212> TYPE: PRT
<213> ORGANISM: Artificial Sequence
<220> FEATURE:
<223> OTHER INFORMATION: Hybrid mouse - human sequence

<400> SEQUENCE: 52

```
Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Gly
                 20                  25                  30

Gly Tyr Tyr Trp Ser Trp Ile Arg Gln His Pro Gly Lys Gly Leu Glu
             35                  40                  45

Trp Ile Gly Tyr Ile His His Ser Ala Gly Thr Tyr Tyr Asn Pro Ser
 50                  55                  60

Leu Lys Ser Arg Val Thr Met Ser Val Asp Thr Ser Lys Asn Gln Leu
 65                  70                  75                  80

Ser Leu Lys Leu Thr Ser Val Thr Ala Ala Asp Thr Ala Val Tyr Tyr
                 85                  90                  95

Cys Ala Arg His Asn Tyr Gly Ser Phe Ala Tyr Trp Gly Gln Gly Thr
                100                 105                 110

Leu Val Thr Val Ser Ser
        115
```

<210> SEQ ID NO 53
<211> LENGTH: 118
<212> TYPE: PRT
<213> ORGANISM: Artificial Sequence
<220> FEATURE:
<223> OTHER INFORMATION: Hybrid mouse - human sequence

<400> SEQUENCE: 53

```
Gln Val Gln Leu Gln Glu Ser Gly Pro Gly Leu Val Lys Pro Ser Glu
  1               5                  10                  15

Thr Leu Ser Leu Thr Cys Ser Val Ser Gly Gly Ser Ile Ser Ser Gly
                 20                  25                  30

Gly Tyr Tyr Trp Ser Trp Ile Arg His His Pro Gly Lys Gly Leu Glu
             35                  40                  45

Trp Ile Gly Tyr Ile His His Ser Ala Gly Thr Tyr Tyr Asn Pro Ser
 50                  55                  60

Leu Lys Ser Arg Val Thr Met Ser Ala Asp Thr Ser Lys Asn Gln Leu
 65                  70                  75                  80

Ser Leu Lys Leu Ala Ser Val Thr Ala Ala Asp Thr Ala Val Tyr Tyr
                 85                  90                  95

Cys Ala Arg His Asn Tyr Gly Ser Phe Ala Tyr Trp Gly Gln Gly Thr
                100                 105                 110

Leu Val Thr Val Ser Ser
        115
```

```
<210> SEQ ID NO 54
<211> LENGTH: 117
<212> TYPE: PRT
<213> ORGANISM: Artificial Sequence
<220> FEATURE:
<223> OTHER INFORMATION: Hybrid mouse - human sequence

<400> SEQUENCE: 54

Gln Val Gln Leu Val Gln Ser Gly Ala Glu Val Arg Lys Pro Gly Ser
 1               5                  10                  15

Ser Val Arg Val Ser Cys Lys Ala Ser Gly Gly Thr Phe Ser Gly Phe
            20                  25                  30

Ala Val Ser Trp Val Arg Gln Ala Pro Gly Gln Arg Phe Glu Trp Leu
        35                  40                  45

Gly Gly Ile Val Ala Ser Leu Gly Ser Thr Asp Tyr Ala Gln Lys Phe
    50                  55                  60

Gln Asp Lys Leu Thr Ile Thr Val Asp Glu Ser Thr Ala Thr Val Tyr
65                  70                  75                  80

Met Glu Met Arg Asn Leu Arg Ser Asp Asp Thr Ala Val Tyr Tyr Cys
                85                  90                  95

Ala Arg His Asn Tyr Gly Ser Phe Ala Tyr Trp Gly Gln Gly Thr Leu
            100                 105                 110

Val Thr Val Ser Ser
        115

<210> SEQ ID NO 55
<211> LENGTH: 109
<212> TYPE: PRT
<213> ORGANISM: Artificial Sequence
<220> FEATURE:
<223> OTHER INFORMATION: hybrid mouse - human sequence

<400> SEQUENCE: 55

Glu Leu Val Met Thr Gln Ser Pro Glu Phe Gln Ser Val Thr Pro Lys
 1               5                  10                  15

Glu Thr Val Thr Ile Thr Cys Arg Ala Ser Gln Asp Ile Gly Asn Ser
            20                  25                  30

Leu His Trp Tyr Gln Gln Lys Pro Gly Gln Ser Pro Lys Leu Leu Ile
        35                  40                  45

Lys Tyr Ala Ser Gln Pro Val Phe Gly Val Pro Ser Arg Phe Arg Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Ser Asn Ser Trp Pro His
                85                  90                  95

Thr Phe Gly Gln Gly Thr Lys Leu Glu Ile Lys Arg Thr
            100                 105

<210> SEQ ID NO 56
<211> LENGTH: 117
<212> TYPE: PRT
<213> ORGANISM: Homo Sapiens
<220> FEATURE:

<400> SEQUENCE: 56

Glu Val Gln Leu Glu Glu Ser Gly Gly Gly Leu Val Lys Pro Gly Gly
 1               5                  10                  15

Ser Leu Lys Leu Ser Cys Ala Ala Ser Gly Phe Ala Phe Ser Ser Tyr
```

-continued

```
                        20                  25                  30
Asp Met Ser Trp Val Arg Gln Ile Pro Glu Lys Arg Leu Glu Trp Val
        35                  40                  45

Ala Lys Val Ser Ser Gly Gly Gly Ser Thr Tyr Tyr Leu Asp Thr Val
    50                  55                  60

Gln Gly Arg Phe Thr Ile Ser Arg Asp Asn Ala Lys Asn Thr Leu Tyr
65                      70                  75                  80

Leu Gln Met Ser Ser Leu Asn Ser Glu Asp Thr Ala Met Tyr Tyr Cys
                85                  90                  95

Ala Arg His Asn Tyr Gly Ser Phe Ala Tyr Trp Gly Gln Gly Thr Leu
            100                 105                 110

Val Thr Val Ser Ala
            115
```

We claim:

1. A method of producing a humanized mouse monoclonal antibody which consists of the steps:

(a) constructing a first human antibody heavy or light chain library consisting of antibody heavy chains or antibody light chains in which each chain in the first human antibody light or heavy chain library has three complementarity determining region (CDR) loops in which the complementarity determining region three (CDR3) loop in each light or heavy chain has the amino acid sequence of a corresponding mouse antibody heavy or light chain CDR3 loop and is flanked by unaltered human framework residues;

(b) constructing a second human antibody heavy or light chain library consisting of antibody heavy chains or antibody light chains, in which each chain in the second human antibody heavy or light chain library has three complementarity determining region (CDR) loops in which the complementarity determining region three (CDR3) loop in each light or heavy chain has the amino acid sequence of a corresponding mouse antibody heavy or light chain CDR3 loop and is flanked by unaltered human framework residues; wherein the chains of said second human antibody heavy or light chain library are the complementary heavy or light chain of said first human antibody heavy or light chain library chains, such that one library is a light chain library and the other library is a heavy chain library;

(c) creating a library of heavy and light chain pairs by combining chains from said first human antibody heavy or light chain library of step (a) with a complementary chain from an antibody which binds a preselected antigen forming a library of heavy and light chain pairs;

(d) isolating antigen binding chains of step (a) by selecting from the library of step (c), a heavy and light chain pair which binds to said preselected antigen, isolating from the antigen binding heavy and light chain pair, the antigen binding chains of step (a);

(e) creating a humanized pair library by combining isolated antigen binding chains of step (d), with chains of said library of step (b), so that a first isolated chain of step (d), together with a complementary second chain in said library of step (b) combine to form a heavy and light chain humanized pair library;

(f) selecting from the humanized pair library of step (e) a humanized heavy and light chain pair that binds to said preselected antigen; and (g) combining two of said selected humanized heavy and light chain pair of step (f) to form a whole antibody; wherein said humanized mouse monoclonal antibody binds the same antigen as the mouse monoclonal antibody.

2. The method of claim 1 wherein the first human antibody heavy or light chain library contains only light chains and the complementary chain is a heavy chain.

3. The method of claim 1 wherein the first human antibody heavy or light chain library contains only heavy chains and the complementary chain is a light chain.

4. The method of claim 1 wherein the heavy chain is a Fd fragment.

5. A method of producing a humanized mouse monoclonal antibody heavy and light chain pair which consists of the steps:

(a) constructing a human light chain library wherein each light chain of said light chain library has three complementarity determining region (CDR) loops in which the complementarity determining region three (CDR3) loop in each light chain has the amino acid sequence of a corresponding mouse antibody light chain CDR3 loop and is flanked by unaltered human framework residues;

(b) selecting a light chain from the light chain library of step (a), wherein the selection comprises combining a heavy chain from an antibody that binds a preselected antigen with a light chain from the library of step (a) to form a heavy and light chain pair library, screening said pair library for binding to said preselected antigen, and isolating light chains that bind to said preselected antigen;

(c) constructing a library of human heavy chains wherein each heavy chain of said library of human heavy chains has three CDR loops in which the complementarity determining region three (CDR3) loop in each heavy chain has the amino acid sequence of a corresponding mouse antibody heavy chain CDR3 loop and is flanked by unaltered human framework residues;

(d) combining a heavy chain from the heavy chain library of step (c) with a selected light chain of step (b) to produce a second library of humanized mouse monoclonal antibody heavy and light chain pairs;

(e) isolating an antigen binding humanized mouse monoclonal antibody heavy and light chain pair from the library of step (d) by screening said library of step (d) for binding with said preselected antigen and isolating those humanized mouse monoclonal antibody heavy and light chain pairs that bind said preselected antigen; wherein said preselected antigen is the same antigen recognized by the mouse monoclonal antibody.

6. The method of claim 5 further comprising converting the selected heavy and light chain pair to a whole antibody.

7. The method of claim 5 wherein the heavy chain of step (b) is a Fd fragment.

8. The method of claim 7 wherein the heavy chain Fd is a humanized mouse heavy chain fragment or a template mouse heavy chain fragment.

9. The method of claim 5 wherein in step (b) a humanized mouse heavy chain is used.

10. The method of claim 5 wherein the CDR3 loop in each light and heavy chain is a CDR3 loop from antibody LM609 produced from hybridoma cell line deposited with American Type Culture Collection under ATCC Accession No. HB 9537.

11. The method of claim 7 wherein the heavy chain Fd is a humanized mouse heavy chain.

12. The method of claim 7 wherein the heavy chain Fd is a template mouse heavy chain fragment.

* * * * *

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

Column 6,
Line 11, "Tbr14" should be -- Thr14 --.

Column 8,
Line 2, "LCDR2" should be -- LCDR1 --.
Line 31, "$\gamma_5$" should be -- $\beta_5$ --.

Column 9,
Line 24, "FL2" should be -- FR2 --.
Line 57, "HR 9537" should be -- HB 9537 --.

Column 44,
Lines 27-29, "wherein said humanized mouse monoclonal antibody binds the same antigen as the mouse monoclonal antibody." should be -- wherein said preselected antigen is the same antigen recognized by the mouse monoclonal antibody. --.

Sequence Listing:
The Sequence Listing depicted at Columns 21-44 should read as follows:

SEQUENCE LISTING

<160> NUMBER OF SEQUENCE ID NOS: 122

<210> SEQ ID NO 1
<211> LENGTH: 8
<212> TYPE: PRT
<213> ORGANISM: Mus Musculus

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<400> SEQUENCE: 1
His Asn Tyr Gly Ser Phe Ala Tyr
 1               5

<210> SEQ ID NO 2
<211> LENGTH: 9
<212> TYPE: PRT
<213> ORGANISM: Mus Musculus

<400> SEQUENCE: 2
Gln Gln Ser Asn Ser Trp Pro His Thr
 1               5

<210> SEQ ID NO 3
<211> LENGTH: 37
<212> TYPE: DNA
<213> ORGANISM: Homo Sapiens

<400> SEQUENCE: 3
gggcccaggc ggccgagctc cagatgaccc agtctcc                    37

<210> SEQ ID NO 4
<211> LENGTH: 37
<212> TYPE: DNA
<213> ORGANISM: Homo Sapiens

<400> SEQUENCE: 4
gggcccaggc ggccgagctc gtgatgacyc agtctcc                    37

<210> SEQ ID NO 5
<211> LENGTH: 37
<212> TYPE: DNA
<213> ORGANISM: Homo Sapiens

<400> SEQUENCE: 5
gggcccaggc ggccgagctc gtgwtgacrc agtctcc                    37
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<210> SEQ ID NO 6
<211> LENGTH: 37
<212> TYPE: DNA
<213> ORGANISM: Homo Sapiens
<400> SEQUENCE: 6
gggcccaggc ggccgagctc acactcacgc agtctcc              37

<210> SEQ ID NO 7
<211> LENGTH: 23
<212> TYPE: DNA
<213> ORGANISM: Homo Sapiens

<400> SEQUENCE: 7
cagtaataca ctgcaaaatc ttc                             23

<210> SEQ ID NO 8
<211> LENGTH: 23
<212> TYPE: DNA
<213> ORGANISM: Homo Sapiens

<400> SEQUENCE: 8
cagtaataaa ccccaacatc ctc                             23

<210> SEQ ID NO 9
<211> LENGTH: 40
<212> TYPE: DNA
<213> ORGANISM: Homo Sapiens

<400> SEQUENCE: 9
gggcccaggc ggccgagctc gtgbtgacgc agccgcctc            40

<210> SEQ ID NO 10
<211> LENGTH: 40
<212> TYPE: DNA
<213> ORGANISM: Homo Sapiens
<400> SEQUENCE: 10
gggcccaggc ggccgagctc gtgctgactc agccaccctc           40
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<210> SEQ ID NO 11
<211> LENGTH: 43
<212> TYPE: DNA
<213> ORGANISM: Homo Sapiens
<400> SEQUENCE: 11
gggcccaggc ggccgagctc gccctgactc agcctccctc cgt        43

<210> SEQ ID NO 12
<211> LENGTH: 46
<212> TYPE: DNA
<213> ORGANISM: Homo Sapiens
<400> SEQUENCE: 12
gggcccaggc ggccgagctc gagctgactc agccaccctc agtgtc     46

<210> SEQ ID NO 13
<211> LENGTH: 40
<212> TYPE: DNA
<213> ORGANISM: Homo Sapiens
<400> SEQUENCE: 13
gggcccaggc ggccgagctc gtgctgactc aatcgccctc           40

<210> SEQ ID NO 14
<211> LENGTH: 40
<212> TYPE: DNA
<213> ORGANISM: Homo Sapiens
<400> SEQUENCE: 14
gggcccaggc ggccgagctc atgctgactc agccccactc           40

<210> SEQ ID NO 15
<211> LENGTH: 40
<212> TYPE: DNA
<213> ORGANISM: Homo Sapiens
<400> SEQUENCE: 15
gggcccaggc ggccgagctc gggcagactc agcagctctc           40
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<210> SEQ ID NO 16
<211> LENGTH: 40
<212> TYPE: DNA
<213> ORGANISM: Homo Sapiens
<400> SEQUENCE: 16
gggcccaggc ggccgagctc gtggtgacyc aggagccmtc                40

<210> SEQ ID NO 17
<211> LENGTH: 40
<212> TYPE: DNA
<213> ORGANISM: Homo Sapiens
<400> SEQUENCE: 17
gggcccaggc ggccgagctc gtgctgactc agccaccttc                40

<210> SEQ ID NO 18
<211> LENGTH: 21
<212> TYPE: DNA
<213> ORGANISM: Homo Sapiens
<400> SEQUENCE: 18
gcagtaataa tcagcctcrt c                                    21

<210> SEQ ID NO 19
<211> LENGTH: 44
<212> TYPE: DNA
<213> ORGANISM: Homo Sapiens
<400> SEQUENCE: 19
gctgcccaac cagccatggc ccaggtgcag ctggtgcagt ctgg           44

<210> SEQ ID NO 20
<211> LENGTH: 44
<212> TYPE: DNA
<213> ORGANISM: Homo Sapiens
<400> SEQUENCE: 20
gctgcccaac cagccatggc ccagatcacc ttgaaggagt ctgg           44
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<210> SEQ ID NO 21
<211> LENGTH: 44
<212> TYPE: DNA
<213> ORGANISM: Homo Sapiens
<400> SEQUENCE: 21
gctgcccaac cagccatggc cgaggtgcag ctggtgaagt ctgg            44

<210> SEQ ID NO 22
<211> LENGTH: 44
<212> TYPE: DNA
<213> ORGANISM: Homo Sapiens
<400> SEQUENCE: 22
gctgcccaac cagccatggc ccaggtgcag ctgcaggagt cggg            44

<210> SEQ ID NO 23
<211> LENGTH: 24
<212> TYPE: DNA
<213> ORGANISM: Homo Sapiens
<400> SEQUENCE: 23
cgcacagtaa tacacggccg tgtc                                  24

<210> SEQ ID NO 24
<211> LENGTH: 21
<212> TYPE: DNA
<213> ORGANISM: Artificial Sequence
<220> FEATURE:
<223> OTHER INFORMATION: PCR Primer for PelB Leader Sequence
<400> SEQUENCE: 24
acctattgcc tacggcagcc g                                     21

<210> SEQ ID NO 25
<211> LENGTH: 24
<212> TYPE: DNA
<213> ORGANISM: Homo Sapiens
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<400> SEQUENCE: 25
cgcacagtaa tacacggccg tgtc                                              24

<210> SEQ ID NO 26
<211> LENGTH: 8
<212> TYPE: PRT
<213> ORGANISM: Homo Sapiens

<400> SEQUENCE: 26
Asp Thr Ala Val Tyr Tyr Cys Ala
 1               5

<210> SEQ ID NO 27
<211> LENGTH: 8
<212> TYPE: PRT
<213> ORGANISM: Mus Musculus

<400> SEQUENCE: 27
Asp Thr Ala Met Tyr Tyr Cys Ala
 1               5

<210> SEQ ID NO 28
<211> LENGTH: 69
<212> TYPE: DNA
<213> ORGANISM: Artificial Sequence
<220> FEATURE:
<223> OTHER INFORMATION: Synthetic PCR Primer
<400> SEQUENCE: 28
gacacggccg tgtattactg tgcgcgtcat aactacggca gttttgctta ctggggccag      60
ggaaccctg                                                              69

<210> SEQ ID NO 29
<211> LENGTH: 42
<212> TYPE: DNA
<213> ORGANISM: Artificial Sequence
```

UNITED STATES PATENT AND TRADEMARK OFFICE
CERTIFICATE OF CORRECTION

PATENT NO. : 7,087,409 B2  
APPLICATION NO. : 10/078757  
DATED : August 8, 2006  
INVENTOR(S) : Carlos F. Barbas, III et al.

Page 8 of 37

It is certified that error appears in the above-identified patent and that said Letters Patent is hereby corrected as shown below:

```
<220> FEATURE:
<223> OTHER INFORMATION: Synthetic PCR Primer

<400> SEQUENCE: 29
gaggaggagg aggagactag ttttgtcaca agatttgggc tc                42

<210> SEQ ID NO 30
<211> LENGTH: 73
<212> TYPE: DNA
<213> ORGANISM: Artificial Sequence
<220> FEATURE:
<223> OTHER INFORMATION: Synthetic PCR Primer
<400> SEQUENCE: 30
gaagattttg cagtgtatta ctgcccaaca gagtaacagc tggcctcaca cgtttggcca  60
ggggaccaag ctg                                                    73

<210> SEQ ID NO 31
<211> LENGTH: 21
<212> TYPE: DNA
<213> ORGANISM: Artificial Sequence
<220> FEATURE:
<223> OTHER INFORMATION: Synthetic PCR Primer
<400> SEQUENCE: 31
aatacgactc actatagggc g                                           21

<210> SEQ ID NO 32
<211> LENGTH: 72
<212> TYPE: DNA
<213> ORGANISM: Artificial Sequence
<220> FEATURE:
<223> OTHER INFORMATION: Synthetic PCR Primer
<400> SEQUENCE: 32
gaggatgttg gggtttatta ctgccaacag agtaacagct ggcctcacac gtttggccag  60
gggaccaagc tg                                                     72
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<210> SEQ ID NO 33
<211> LENGTH: 8
<212> TYPE: PRT
<213> ORGANISM: Homo Sapiens
<400> SEQUENCE: 33
Glu Asp Phe Ala Val Tyr Tyr Cys
 1               5

<210> SEQ ID NO 34
<211> LENGTH: 8
<212> TYPE: PRT
<213> ORGANISM: Homo Sapiens

<400> SEQUENCE: 34
Glu Asp Val Gly Val Tyr Tyr Cys
 1               5

<210> SEQ ID NO 35
<211> LENGTH: 69
<212> TYPE: DNA
<213> ORGANISM: Artificial Sequence
<220> FEATURE:
<223> OTHER INFORMATION: Synthetic PCR Primer
<400> SEQUENCE: 35
gaygaggctg attattactg ccaacagagt aacagctggc ctcacacgtt cggcggaggg    60
accaagctg                                                            69

<210> SEQ ID NO 36
<211> LENGTH: 50
<212> TYPE: DNA
<213> ORGANISM: Artificial Sequence
<220> FEATURE:
<223> OTHER INFORMATION: Synthetic PCR Primer
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<400> SEQUENCE: 36
agagagagag agagagagag cgccgtctag aattatgaac attctgtagg        50

<210> SEQ ID NO 37
<211> LENGTH: 7
<212> TYPE: PRT
<213> ORGANISM: Homo Sapiens

<400> SEQUENCE: 37
Asp Glu Ala Asp Tyr Tyr Cys
 1               5

<210> SEQ ID NO 38
<211> LENGTH: 7
<212> TYPE: PRT
<213> ORGANISM: Homo Sapiens

<400> SEQUENCE: 38
Phe Gly Gly Gly Thr Lys Leu
 1               5

<210> SEQ ID NO 39
<211> LENGTH: 22
<212> TYPE: DNA
<213> ORGANISM: Artificial Sequence
<220> FEATURE:
<223> OTHER INFORMATION: Synthetic PCR Primer
<400> SEQUENCE: 39
aagacagcta tcgcgattgc ag                                      22

<210> SEQ ID NO 40
<211> LENGTH: 41
<212> TYPE: DNA
<213> ORGANISM: Artificial Sequence
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<220> FEATURE:
<223> OTHER INFORMATION: Synthetic PCR Primer

<400> SEQUENCE: 40
gaggaggagg aggaggaggc ggggcccagg cggccgagct c        41

<210> SEQ ID NO 41
<211> LENGTH: 21
<212> TYPE: DNA
<213> ORGANISM: Artificial Sequence
<220> FEATURE:
<223> OTHER INFORMATION: Synthetic PCR Primer
<400> SEQUENCE: 41
ggccatggct ggttgggcag c                              21

<210> SEQ ID NO 42
<211> LENGTH: 42
<212> TYPE: DNA
<213> ORGANISM: Artificial Sequence
<220> FEATURE:
<223> OTHER INFORMATION: Synthetic PCR Primer
<400> SEQUENCE: 42
gcagagccca aatcttgtga cactagtggc caggccggcc ag       42

<210> SEQ ID NO 43
<211> LENGTH: 41
<212> TYPE: DNA
<213> ORGANISM: Artificial Sequence
<220> FEATURE:
<223> OTHER INFORMATION: Synthetic PCR Primer
<400> SEQUENCE: 43
gaggaggagg aggaggagcc tggccggcct ggccactagt g        41
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<210> SEQ ID NO 44
<211> LENGTH: 130
<212> TYPE: PRT
<213> ORGANISM: Mus Musculus
<400> SEQUENCE: 44
Leu Glu Glu Ser Gly Gly Gly Leu Val Lys Pro Gly Gly Ser Leu Lys
1               5                   10                  15
Leu Ser Cys Ala Ala Ser Gly Phe Ala Phe Ser Ser Tyr Asp Met Ser
            20                  25                  30
Trp Val Arg Gln Ile Pro Glu Lys Arg Leu Glu Trp Val Ala Lys Val
        35                  40                  45
Ser Ser Gly Gly Gly Ser Thr Tyr Tyr Leu Asp Thr Val Gln Gly Arg
    50                  55                  60
Phe Thr Ile Ser Arg Asp Asn Ala Lys Asn Thr Leu Tyr Leu Gln Met
65                  70                  75                  80
Ser Ser Leu Asn Ser Glu Asp Thr Ala Met Tyr Tyr Cys Ala Arg His
                85                  90                  95
Asn Tyr Gly Ser Phe Ala Tyr Trp Gly Gln Gly Thr Leu Val Thr Val
                100                 105                 110
Ser Ala Ala Lys Thr Thr Pro Pro Ser Val Tyr Pro Leu Ala Pro Gly
            115                 120                 125
Ser Ala
    130

<210> SEQ ID NO 45
<211> LENGTH: 109
<212> TYPE: PRT
<213> ORGANISM: Mus Musculus
<400> SEQUENCE: 45
Glu Leu Val Met Thr Gln Thr Pro Ala Thr Leu Ser Val Thr Pro Gly
1               5                   10                  15
Asp Ser Val Ser Leu Ser Cys Arg Ala Ser Gln Ser Ile Ser Asn His
            20                  25                  30
Leu His Trp Tyr Gln Gln Lys Ser His Glu Ser Pro Arg Leu Leu Ile
        35                  40                  45
Lys Tyr Ala Ser Gln Ser Ile Ser Gly Ile Pro Ser Arg Phe Ser Gly
    50                  55                  60
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
Ser Gly Ser Gly Thr Asp Phe Thr Leu Ser Ile Asn Ser Val Glu Thr
 65                  70                  75                  80
Glu Asp Phe Gly Met Tyr Phe Cys Gln Gln Ser Asn Ser Trp Pro His
                 85                  90                  95
Thr Phe Gly Gly Gly Thr Lys Leu Glu Ile Lys Arg Ala
                100                 105

<210> SEQ ID NO 46
<211> LENGTH: 57
<212> TYPE: DNA
<213> ORGANISM: Artificial Sequence
<220> FEATURE:
<223> OTHER INFORMATION: Synthetic PCR Primer
<221> NAME/KEY: misc_feature
<222> LOCATION: (1)...(57)
<223> OTHER INFORMATION: n= A, T, C, or G
<400> SEQUENCE: 46
ggtccctgg ccaaacgtgt gaggmnnmnn mnnmnnctgt tggcagtaat acactgc       57

<210> SEQ ID NO 47
<211> LENGTH: 23
<212> TYPE: DNA
<213> ORGANISM: Artificial Sequence
<220> FEATURE:
<223> OTHER INFORMATION: Synthetic PCR Primer
<400> SEQUENCE: 47
cctcaccgtt tggccagggg acc                                          23

<210> SEQ ID NO 48
<211> LENGTH: 21
<212> TYPE: DNA
<213> ORGANISM: Artificial Sequence
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<220> FEATURE:
<223> OTHER INFORMATION: Synthetic PCR Primer

<400> SEQUENCE: 48
agaagcgtag tccggaacgt c                                           21

<210> SEQ ID NO 49
<211> LENGTH: 109
<212> TYPE: PRT
<213> ORGANISM: Artificial Sequence
<220> FEATURE:
<223> OTHER INFORMATION: Hybrid mouse - human sequence
<400> SEQUENCE: 49
Glu Leu Val Met Thr Gln Ser Pro Glu Phe Gln Ser Val Thr Pro Lys
 1               5                  10                  15
Glu Thr Val Thr Ile Thr Cys Arg Ala Ser Gln Asp Ile Gly Thr Ser
                20                  25                  30
Leu His Trp Tyr Gln Gln Lys Pro Gly Gln Ser Pro Lys Leu Leu Ile
                35                  40                  45
Lys Tyr Ala Ser Gln Pro Val Phe Gly Val Pro Ser Arg Phe Arg Gly
            50                  55                  60
Ser Gly Ser Gly Thr Asp Phe Thr Leu Thr Ile Tyr Ser Leu Glu Ala
65                  70                  75                  80
Glu Asp Phe Ala Val Tyr Tyr Cys Gln Gln Ser Asn Ser Trp Pro His
                85                  90                  95
Thr Phe Gly Gln Gly Thr Lys Leu Glu Ile Lys Arg Thr
               100                 105

<210> SEQ ID NO 50
<211> LENGTH: 118
<212> TYPE: PRT
<213> ORGANISM: Artificial Sequence
<220> FEATURE:
<223> OTHER INFORMATION: Hybrid mouse - human sequence

<400> SEQUENCE: 50
```

UNITED STATES PATENT AND TRADEMARK OFFICE
CERTIFICATE OF CORRECTION

PATENT NO.       : 7,087,409 B2
APPLICATION NO.  : 10/078757
DATED            : August 8, 2006
INVENTOR(S)      : Carlos F. Barbas, III et al.

It is certified that error appears in the above-identified patent and that said Letters Patent is hereby corrected as shown below:

```
Gln Val Gln Leu Gln Glu Ser Gly Pro Gly Leu Val Lys Pro Ser Gln
 1               5                  10                  15
Thr Leu Ser Leu Thr Cys Thr Val Ser Gly Ala Ser Ile Ser Arg Gly
             20                  25                  30
Gly Tyr Tyr Trp Ser Trp Ile Arg Gln Tyr Pro Gly Lys Gly Leu Glu
             35                  40                  45
Trp Ile Gly Tyr Ile His His Ser Gly Ser Thr Tyr Tyr Asn Pro Ser
 50                  55                  60
Leu Lys Ser Arg Val Thr Ile Ala Ile Asp Thr Ser Lys Asn Gln Leu
 65                  70                  75                  80
Ser Leu Arg Leu Thr Ser Val Thr Ala Ala Asp Thr Ala Val Tyr Tyr
             85                  90                  95
Cys Ala Arg His Asn Tyr Gly Ser Phe Ala Tyr Trp Gly Gln Gly Thr
            100                 105                 110
Leu Val Thr Val Ser Ser
            115

<210> SEQ ID NO 51
<211> LENGTH: 118
<212> TYPE: PRT
<213> ORGANISM: Artificial Sequence
<220> FEATURE:
<223> OTHER INFORMATION: Hybrid mouse - human sequence
<400> SEQUENCE: 51
Gln Val Gln Leu Gln Glu Ser Gly Pro Gly Leu Val Lys Pro Ser Gln
 1               5                  10                  15
Thr Leu Phe Leu Thr Cys Thr Val Ser Gly Gly Ser Ile Ser Ser Gly
             20                  25                  30
Gly Tyr Tyr Trp Ser Trp Ile Arg His His Pro Gly Lys Gly Leu Glu
             35                  40                  45
Trp Ile Gly Tyr Ile His His Arg Ala Ala Pro Tyr Tyr Asn Pro Ser
 50                  55                  60
Leu Lys Ser Arg Val Thr Ile Ser Val Asp Thr Ser Arg Asn Gln Ile
 65                  70                  75                  80
Ser Leu Lys Leu Arg Ser Val Thr Ala Ala Asp Thr Ala Val Tyr Tyr
             85                  90                  95
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
           Cys Ala Arg His Asn Tyr Gly Ser Phe Ala Tyr Trp Gly Gln Gly Thr
                       100                 105                 110
           Leu Val Thr Val Ser Ser
                       115

<210> SEQ ID NO 52
    <211> LENGTH: 118
    <212> TYPE: PRT
    <213> ORGANISM: Artificial Sequence
<220> FEATURE:
    <223> OTHER INFORMATION: Hybrid mouse - human sequence
<400> SEQUENCE: 52
    Gln Val Gln Leu Gln Glu Ser Gly Pro Gly Leu Val Lys Pro Ser Glu
    1               5                   10                  15
    Thr Leu Ser Leu Thr Cys Thr Val Ser Gly Gly Ser Ile Ser Ser Gly
                    20                  25                  30
    Gly Tyr Tyr Trp Ser Trp Ile Arg Gln His Pro Gly Lys Gly Leu Glu
                35                  40                  45
    Trp Ile Gly Tyr Ile His His Ser Ala Gly Thr Tyr Tyr Asn Pro Ser
        50                  55                  60
    Leu Lys Ser Arg Val Thr Met Ser Val Asp Thr Ser Lys Asn Gln Leu
    65                  70                  75                  80
    Ser Leu Lys Leu Thr Ser Val Thr Ala Ala Asp Thr Ala Val Tyr Tyr
                    85                  90                  95
    Cys Ala Arg His Asn Tyr Gly Ser Phe Ala Tyr Trp Gly Gln Gly Thr
                        100                 105                 110
    Leu Val Thr Val Ser Ser
                115

<210> SEQ ID NO 53
    <211> LENGTH: 118
    <212> TYPE: PRT
    <213> ORGANISM: Artificial Sequence
<220> FEATURE:
    <223> OTHER INFORMATION: Hybrid mouse - human sequence
```

UNITED STATES PATENT AND TRADEMARK OFFICE
CERTIFICATE OF CORRECTION

PATENT NO. : 7,087,409 B2  
APPLICATION NO. : 10/078757  
DATED : August 8, 2006  
INVENTOR(S) : Carlos F. Barbas, III et al.

It is certified that error appears in the above-identified patent and that said Letters Patent is hereby corrected as shown below:

```
<400> SEQUENCE: 53
Gln Val Gln Leu Gln Glu Ser Gly Pro Gly Leu Val Lys Pro Ser Glu
1               5                   10                  15
Thr Leu Ser Leu Thr Cys Ser Val Ser Gly Gly Ser Ile Ser Ser Gly
            20                  25                  30
Gly Tyr Tyr Trp Ser Trp Ile Arg His His Pro Gly Lys Gly Leu Glu
        35                  40                  45
Trp Ile Gly Tyr Ile His His Ser Ala Gly Thr Tyr Tyr Asn Pro Ser
    50                  55                  60
Leu Lys Ser Arg Val Thr Met Ser Ala Asp Thr Ser Lys Asn Gln Leu
65                  70                  75                  80
Ser Leu Lys Leu Ala Ser Val Thr Ala Ala Asp Thr Ala Val Tyr Tyr
                85                  90                  95
Cys Ala Arg His Asn Tyr Gly Ser Phe Ala Tyr Trp Gly Gln Gly Thr
            100                 105                 110
Leu Val Thr Val Ser Ser
            115

<210> SEQ ID NO 54
<211> LENGTH: 117
<212> TYPE: PRT
<213> ORGANISM: Artificial Sequence
<220> FEATURE:
<223> OTHER INFORMATION: Hybrid mouse - human sequence
<400> SEQUENCE: 54
Gln Val Gln Leu Val Gln Ser Gly Ala Glu Val Arg Lys Pro Gly Ser
1               5                   10                  15
Ser Val Arg Val Ser Cys Lys Ala Ser Gly Gly Thr Phe Ser Gly Phe
            20                  25                  30
Ala Val Ser Trp Val Arg Gln Ala Pro Gly Gln Arg Phe Glu Trp Leu
        35                  40                  45
Gly Gly Ile Val Ala Ser Leu Gly Ser Thr Asp Tyr Ala Gln Lys Phe
    50                  55                  60
Gln Asp Lys Leu Thr Ile Thr Val Asp Glu Ser Thr Ala Thr Val Tyr
65                  70                  75                  80
Met Glu Met Arg Asn Leu Arg Ser Asp Asp Thr Ala Val Tyr Tyr Cys
                85                  90                  95
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
Ala Arg His Asn Tyr Gly Ser Phe Ala Tyr Trp Gly Gln Gly Thr Leu
                100                 105                 110
Val Thr Val Ser Ser
            115

<210> SEQ ID NO 55
<211> LENGTH: 109
<212> TYPE: PRT
<213> ORGANISM: Artificial Sequence
<220> FEATURE:
<223> OTHER INFORMATION: Hybrid mouse - human sequence
<400> SEQUENCE: 55
Glu Leu Val Met Thr Gln Ser Pro Glu Phe Gln Ser Val Thr Pro Lys
 1               5                  10                  15
Glu Thr Val Thr Ile Thr Cys Arg Ala Ser Gln Asp Ile Gly Asn Ser
            20                  25                  30
Leu His Trp Tyr Gln Gln Lys Pro Gly Gln Ser Pro Lys Leu Leu Ile
        35                  40                  45
Lys Tyr Ala Ser Gln Pro Val Phe Gly Val Pro Ser Arg Phe Arg Gly
    50                  55                  60
Ser Gly Ser Gly Thr Asp Phe Thr Leu Thr Ile Ser Arg Leu Glu Pro
65                  70                  75                  80
Glu Asp Phe Ala Val Tyr Tyr Cys Gln Gln Ser Asn Ser Trp Pro His
                85                  90                  95
Thr Phe Gly Gln Gly Thr Lys Leu Glu Ile Lys Arg Thr
                100                 105

<210> SEQ ID NO 56
<211> LENGTH: 117
<212> TYPE: PRT
<213> ORGANISM: Homo Sapiens
<400> SEQUENCE: 56
Glu Val Gln Leu Glu Glu Ser Gly Gly Gly Leu Val Lys Pro Gly Gly
 1               5                  10                  15
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
Ser Leu Lys Leu Ser Cys Ala Ala Ser Gly Phe Ala Phe Ser Ser Tyr
            20                  25                  30
Asp Met Ser Trp Val Arg Gln Ile Pro Glu Lys Arg Leu Glu Trp Val
        35                  40                  45
Ala Lys Val Ser Ser Gly Gly Gly Ser Thr Tyr Tyr Leu Asp Thr Val
    50                  55                  60
Gln Gly Arg Phe Thr Ile Ser Arg Asp Asn Ala Lys Asn Thr Leu Tyr
65                  70                  75                  80
Leu Gln Met Ser Ser Leu Asn Ser Glu Asp Thr Ala Met Tyr Tyr Cys
                85                  90                  95
Ala Arg His Asn Tyr Gly Ser Phe Ala Tyr Trp Gly Gln Gly Thr Leu
                100                 105                 110
Val Thr Val Ser Ala
            115
```

```
<210> SEQ ID NO 57
<211> LENGTH: 4
<212> TYPE: PRT
<213> ORGANISM: Homo Sapiens
<400> SEQUENCE: 57
Glu Arg Ala Thr
 1

<210> SEQ ID NO 58
<211> LENGTH: 4
<212> TYPE: PRT
<213> ORGANISM: Homo Sapiens

<400> SEQUENCE: 58
Glu Arg Gly Ser
 1

<210> SEQ ID NO 59
<211> LENGTH: 5
<212> TYPE: PRT
<213> ORGANISM: Homo Sapiens
```

UNITED STATES PATENT AND TRADEMARK OFFICE
CERTIFICATE OF CORRECTION

| | |
|---|---|
| PATENT NO. | : 7,087,409 B2 |
| APPLICATION NO. | : 10/078757 |
| DATED | : August 8, 2006 |
| INVENTOR(S) | : Carlos F. Barbas, III et al. |

It is certified that error appears in the above-identified patent and that said Letters Patent is hereby corrected as shown below:

```
<400> SEQUENCE: 59
Ser Ser Thr Leu Ala
 1               5

<210> SEQ ID NO 60
<211> LENGTH: 5
<212> TYPE: PRT
<213> ORGANISM: Homo Sapiens

<400> SEQUENCE: 60
Ser Ser Phe Leu Ala
 1               5

<210> SEQ ID NO 61
<211> LENGTH: 7
<212> TYPE: PRT
<213> ORGANISM: Homo Sapiens

<400> SEQUENCE: 61
Val Thr Ser Ser Tyr Leu Ala
 1               5

<210> SEQ ID NO 62
<211> LENGTH: 4
<212> TYPE: PRT
<213> ORGANISM: Homo Sapiens

<400> SEQUENCE: 62
Pro Gly Gln Ala
 1

<210> SEQ ID NO 63
<211> LENGTH: 4
<212> TYPE: PRT
<213> ORGANISM: Homo Sapiens
```

UNITED STATES PATENT AND TRADEMARK OFFICE
CERTIFICATE OF CORRECTION

PATENT NO.       : 7,087,409 B2
APPLICATION NO.  : 10/078757
DATED            : August 8, 2006
INVENTOR(S)      : Carlos F. Barbas, III et al.

It is certified that error appears in the above-identified patent and that said Letters Patent is hereby corrected as shown below:

```
    <400> SEQUENCE: 63
    Pro Gly Lys Ala
     1

<210> SEQ ID NO 64
    <211> LENGTH: 4
    <212> TYPE: PRT
    <213> ORGANISM: Homo Sapiens
<400> SEQUENCE: 64
    Ser Arg Ala Thr
     1

<210> SEQ ID NO 65
    <211> LENGTH: 8
    <212> TYPE: PRT
    <213> ORGANISM: Mus Musculus
<400> SEQUENCE: 65
    Arg Ala Ser Gln Ser Ile Ser Asn
     1                   5

<210> SEQ ID NO 66
    <211> LENGTH: 8
    <212> TYPE: PRT
    <213> ORGANISM: Mus Musculus
<400> SEQUENCE: 66
    Lys Tyr Ala Ser Gln Ser Ile Ser
     1                   5

<210> SEQ ID NO 67
    <211> LENGTH: 8
    <212> TYPE: PRT
    <213> ORGANISM: Homo Sapiens
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<400> SEQUENCE: 67
Arg Ala Ser Gln Asp Ile Gly Thr
1               5

<210> SEQ ID NO 68
<211> LENGTH: 8
<212> TYPE: PRT
<213> ORGANISM: Homo Sapiens

<400> SEQUENCE: 68
Lys Tyr Ala Ser Gln Pro Val Phe
1               5

<210> SEQ ID NO 69
<211> LENGTH: 8
<212> TYPE: PRT
<213> ORGANISM: Homo Sapiens

<400> SEQUENCE: 69
Arg Ala Ser Gln Asp Ile Gly Asn
1               5

<210> SEQ ID NO 70
<211> LENGTH: 8
<212> TYPE: PRT
<213> ORGANISM: Homo Sapiens

<400> SEQUENCE: 70
Arg Ala Ser Gln Ser Ile Gly Trp
1               5

<210> SEQ ID NO 71
<211> LENGTH: 8
<212> TYPE: PRT
<213> ORGANISM: Homo Sapiens
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<400> SEQUENCE: 71
Lys Tyr Ala Ser Gln Ser Ile Ser
 1               5

<210> SEQ ID NO 72
<211> LENGTH: 8
<212> TYPE: PRT
<213> ORGANISM: Homo Sapiens

<400> SEQUENCE: 72
Arg Ser Ser Gln Ser Ile Asn Ile
 1               5

<210> SEQ ID NO 73
<211> LENGTH: 8
<212> TYPE: PRT
<213> ORGANISM: Homo Sapiens

<400> SEQUENCE: 73
Tyr His Ala Ser Lys Arg Ala Ser
 1               5

<210> SEQ ID NO 74
<211> LENGTH: 9
<212> TYPE: PRT
<213> ORGANISM: Homo Sapiens

<400> SEQUENCE: 74
Arg Ala Ser Gln Ser Val Ser Asn Asn
 1               5

<210> SEQ ID NO 75
<211> LENGTH: 8
<212> TYPE: PRT
<213> ORGANISM: Homo Sapiens
```

UNITED STATES PATENT AND TRADEMARK OFFICE
CERTIFICATE OF CORRECTION

PATENT NO. : 7,087,409 B2  Page 24 of 37
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<400> SEQUENCE: 75
Tyr Arg Ala Ser Ser Arg Ala Thr
 1               5

<210> SEQ ID NO 76
<211> LENGTH: 13
<212> TYPE: PRT
<213> ORGANISM: Homo Sapiens
<400> SEQUENCE: 76
Arg Ser Ser Gln Ser Leu Val Tyr Ser Asp Gly Asn Thr
 1               5                  10

<210> SEQ ID NO 77
<211> LENGTH: 8
<212> TYPE: PRT
<213> ORGANISM: Homo Sapiens

<400> SEQUENCE: 77
Tyr Lys Val Ser Asn Arg Asp Ser
 1               5

<210> SEQ ID NO 78
<211> LENGTH: 13
<212> TYPE: PRT
<213> ORGANISM: Homo Sapiens
<400> SEQUENCE: 78
Tyr Ala Ser Gln Ser Leu Val Tyr Thr Asp Gly Asn Thr
 1               5                  10

<210> SEQ ID NO 79
<211> LENGTH: 8
<212> TYPE: PRT
<213> ORGANISM: Homo Sapiens
```

UNITED STATES PATENT AND TRADEMARK OFFICE
CERTIFICATE OF CORRECTION

PATENT NO.       : 7,087,409 B2
APPLICATION NO.  : 10/078757
DATED            : August 8, 2006
INVENTOR(S)      : Carlos F. Barbas, III et al.

It is certified that error appears in the above-identified patent and that said Letters Patent is hereby corrected as shown below:

```
<400> SEQUENCE: 79
Tyr Met Val Ser Asn Arg Asp Ser
1               5

<210> SEQ ID NO 80
<211> LENGTH: 23
<212> TYPE: PRT
<213> ORGANISM: Mus Musculus
<400> SEQUENCE: 80
Glu Leu Val Met Thr Gln Thr Pro Ala Thr Leu Ser Val Thr Pro Gly
1               5                  10                  15
Asp Ser Val Ser Leu Ser Cys
            20

<210> SEQ ID NO 81
<211> LENGTH: 23
<212> TYPE: PRT
<213> ORGANISM: Homo Sapiens
<400> SEQUENCE: 81
Glu Leu Val Met Thr Gln Ser Pro Glu Phe Gln Ser Val Thr Pro Lys
1               5                  10                  15
Glu Thr Val Thr Ile Thr Cys
            20

<210> SEQ ID NO 82
<211> LENGTH: 11
<212> TYPE: PRT
<213> ORGANISM: Mus Musculus
<400> SEQUENCE: 82
Arg Ala Ser Gln Ser Ile Ser Asn His Leu His
1               5                  10
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<210> SEQ ID NO 83
<211> LENGTH: 11
<212> TYPE: PRT
<213> ORGANISM: Homo Sapiens
<400> SEQUENCE: 83
Arg Ala Ser Gln Asp Ile Gly Thr Ser Leu His
 1               5                  10

<210> SEQ ID NO 84
<211> LENGTH: 11
<212> TYPE: PRT
<213> ORGANISM: Homo Sapiens
<400> SEQUENCE: 84
Arg Ala Ser Gln Asp Ile Gly Asn Ser Leu His
 1               5                  10

<210> SEQ ID NO 85
<211> LENGTH: 15
<212> TYPE: PRT
<213> ORGANISM: Mus Musculus
<400> SEQUENCE: 85
Trp Tyr Gln Gln Lys Ser His Glu Ser Pro Arg Leu Leu Ile Lys
 1               5                  10                  15

<210> SEQ ID NO 86
<211> LENGTH: 15
<212> TYPE: PRT
<213> ORGANISM: Homo Sapiens
<400> SEQUENCE: 86
Trp Tyr Gln Gln Lys Pro Gly Gln Ser Pro Lys Leu Leu Ile Lys
 1               5                  10                  15
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<210> SEQ ID NO 87
<211> LENGTH: 7
<212> TYPE: PRT
<213> ORGANISM: Mus Musculus
<400> SEQUENCE: 87
Tyr Ala Ser Gln Ser Ile Ser
 1               5

<210> SEQ ID NO 88
<211> LENGTH: 7
<212> TYPE: PRT
<213> ORGANISM: Homo Sapiens

<400> SEQUENCE: 88
Tyr Ala Ser Gln Pro Val Phe
 1               5

<210> SEQ ID NO 89
<211> LENGTH: 32
<212> TYPE: PRT
<213> ORGANISM: Mus Musculus
<400> SEQUENCE: 89
Gly Ile Pro Ser Arg Phe Ser Gly Ser Gly Ser Gly Thr Asp Phe Thr
 1               5                  10                  15
Leu Ser Ile Asn Ser Val Glu Thr Glu Asp Phe Gly Met Tyr Phe Cys
                 20                  25                  30

<210> SEQ ID NO 90
<211> LENGTH: 32
<212> TYPE: PRT
<213> ORGANISM: Homo Sapiens
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<400> SEQUENCE: 90
Gly Val Pro Ser Arg Phe Arg Gly Ser Gly Ser Gly Thr Asp Phe Thr
1               5                   10                  15
Leu Thr Ile Tyr Ser Leu Glu Ala Glu Asp Phe Ala Val Tyr Tyr Cys
                20                  25                  30

<210> SEQ ID NO 91
<211> LENGTH: 32
<212> TYPE: PRT
<213> ORGANISM: Homo Sapiens
<400> SEQUENCE: 91
Gly Val Pro Ser Arg Phe Arg Gly Ser Gly Ser Gly Thr Asp Phe Thr
1               5                   10                  15
Leu Thr Ile Ser Arg Leu Glu Pro Glu Asp Phe Ala Val Tyr Tyr Cys
                20                  25                  30

<210> SEQ ID NO 92
<211> LENGTH: 12
<212> TYPE: PRT
<213> ORGANISM: Mus Musculus
<400> SEQUENCE: 92
Phe Gly Gly Gly Thr Lys Leu Glu Ile Lys Arg Ala
1               5                   10

<210> SEQ ID NO 93
<211> LENGTH: 12
<212> TYPE: PRT
<213> ORGANISM: Homo Sapiens
<400> SEQUENCE: 93
Phe Gly Gln Gly Thr Lys Leu Glu Ile Lys Arg Thr
1               5                   10
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<210> SEQ ID NO 94
<211> LENGTH: 30
<212> TYPE: PRT
<213> ORGANISM: Mus Musculus
<400> SEQUENCE: 94
Glu Val Gln Leu Glu Glu Ser Gly Gly Gly Leu Val Lys Pro Gly Gly
 1               5                  10                  15
Ser Leu Lys Leu Ser Cys Ala Ala Ser Gly Phe Ala Phe Ser
            20                  25                  30

<210> SEQ ID NO 95
<211> LENGTH: 30
<212> TYPE: PRT
<213> ORGANISM: Homo Sapiens
<400> SEQUENCE: 95
Gln Val Gln Leu Val Gln Ser Gly Ala Glu Val Arg Lys Pro Gly Ser
 1               5                  10                  15
Ser Val Arg Val Ser Cys Lys Ala Ser Gly Gly Thr Phe Ser
            20                  25                  30

<210> SEQ ID NO 96
<211> LENGTH: 30
<212> TYPE: PRT
<213> ORGANISM: Homo Sapiens
<400> SEQUENCE: 96
Gln Val Gln Leu Gln Glu Ser Gly Pro Gly Leu Val Lys Pro Ser Gln
 1               5                  10                  15
Thr Leu Ser Leu Thr Cys Thr Val Ser Gly Ala Ser Ile Ser
            20                  25                  30

<210> SEQ ID NO 97
<211> LENGTH: 30
<212> TYPE: PRT
<213> ORGANISM: Homo Sapiens
```

UNITED STATES PATENT AND TRADEMARK OFFICE
CERTIFICATE OF CORRECTION

PATENT NO.       : 7,087,409 B2
APPLICATION NO.  : 10/078757
DATED            : August 8, 2006
INVENTOR(S)      : Carlos F. Barbas, III et al.

It is certified that error appears in the above-identified patent and that said Letters Patent is hereby corrected as shown below:

```
<400> SEQUENCE: 97
Gln Val Gln Leu Gln Glu Ser Gly Pro Gly Leu Val Lys Pro Ser Gln
 1               5                  10                  15
Thr Leu Phe Leu Thr Cys Thr Val Ser Gly Gly Ser Ile Ser
             20                  25                  30

<210> SEQ ID NO 98
<211> LENGTH: 30
<212> TYPE: PRT
<213> ORGANISM: Homo Sapiens
<400> SEQUENCE: 98
Gln Val Gln Leu Gln Glu Ser Gly Pro Gly Leu Val Lys Pro Ser Glu
 1               5                  10                  15
Thr Leu Ser Leu Thr Cys Thr Val Ser Gly Gly Ser Ile Ser
             20                  25                  30

<210> SEQ ID NO 99
<211> LENGTH: 30
<212> TYPE: PRT
<213> ORGANISM: Homo Sapiens
<400> SEQUENCE: 99
Gln Val Gln Leu Gln Glu Ser Gly Pro Gly Leu Val Lys Pro Ser Glu
 1               5                  10                  15
Thr Leu Ser Leu Thr Cys Ser Val Ser Gly Gly Ser Ile Ser
             20                  25                  30

<210> SEQ ID NO 100
<211> LENGTH: 5
<212> TYPE: PRT
<213> ORGANISM: Mus Musculus
<400> SEQUENCE: 100
Ser Tyr Asp Met Ser
 1               5
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<210> SEQ ID NO 101
<211> LENGTH: 5
<212> TYPE: PRT
<213> ORGANISM: Homo Sapiens
<400> SEQUENCE: 101
Gly Phe Ala Val Ser
 1               5

<210> SEQ ID NO 102
<211> LENGTH: 7
<212> TYPE: PRT
<213> ORGANISM: Homo Sapiens
<400> SEQUENCE: 102
Arg Gly Gly Tyr Tyr Trp Ser
 1               5

<210> SEQ ID NO 103
<211> LENGTH: 7
<212> TYPE: PRT
<213> ORGANISM: Homo Sapiens
<400> SEQUENCE: 103
Ser Gly Gly Tyr Tyr Trp Ser
 1               5

<210> SEQ ID NO 104
<211> LENGTH: 14
<212> TYPE: PRT
<213> ORGANISM: Mus Musculus
<400> SEQUENCE: 104
Trp Val Arg Gln Ile Pro Glu Lys Arg Leu Glu Trp Val Ala
 1               5                  10
```

UNITED STATES PATENT AND TRADEMARK OFFICE
CERTIFICATE OF CORRECTION

PATENT NO.         : 7,087,409 B2
APPLICATION NO.    : 10/078757
DATED              : August 8, 2006
INVENTOR(S)        : Carlos F. Barbas, III et al.

It is certified that error appears in the above-identified patent and that said Letters Patent is hereby corrected as shown below:

```
<210> SEQ ID NO 105
<211> LENGTH: 14
<212> TYPE: PRT
<213> ORGANISM: Homo Sapiens
<400> SEQUENCE: 105
Trp Val Arg Gln Ala Pro Gly Gln Arg Phe Glu Trp Leu Gly
 1               5                  10

<210> SEQ ID NO 106
<211> LENGTH: 14
<212> TYPE: PRT
<213> ORGANISM: Homo Sapiens
<400> SEQUENCE: 106
Trp Ile Arg Gln Tyr Pro Gly Lys Gly Leu Glu Trp Ile Gly
 1               5                  10

<210> SEQ ID NO 107
<211> LENGTH: 14
<212> TYPE: PRT
<213> ORGANISM: Homo Sapiens
<400> SEQUENCE: 107
Trp Ile Arg His His Pro Gly Lys Gly Leu Glu Trp Ile Gly
 1               5                  10

<210> SEQ ID NO 108
<211> LENGTH: 14
<212> TYPE: PRT
<213> ORGANISM: Homo Sapiens
<400> SEQUENCE: 108
Trp Ile Arg Gln His Pro Gly Lys Gly Leu Glu Trp Ile Gly
 1               5                  10
```

UNITED STATES PATENT AND TRADEMARK OFFICE
CERTIFICATE OF CORRECTION

PATENT NO.        : 7,087,409 B2
APPLICATION NO.   : 10/078757
DATED             : August 8, 2006
INVENTOR(S)       : Carlos F. Barbas, III et al.

It is certified that error appears in the above-identified patent and that said Letters Patent is hereby corrected as shown below:

```
<210> SEQ ID NO 109
<211> LENGTH: 17
<212> TYPE: PRT
<213> ORGANISM: Homo Sapiens
<400> SEQUENCE: 109
Gly Ile Val Ala Ser Leu Gly Ser Thr Asp Tyr Ala Gln Lys Phe Gln
 1               5                  10                  15
Asp <210> SEQ ID NO 110
<211> LENGTH: 16
<212> TYPE: PRT
<213> ORGANISM: Homo Sapiens
<400> SEQUENCE: 110
Tyr Ile His His Ser Gly Ser Thr Tyr Tyr Asn Pro Ser Leu Lys Ser
 1               5                  10                  15

<210> SEQ ID NO 111
<211> LENGTH: 16
<212> TYPE: PRT
<213> ORGANISM: Homo Sapiens
<400> SEQUENCE: 111
Tyr Ile His His Arg Ala Ala Pro Tyr Tyr Asn Pro Ser Leu Lys Ser
 1               5                  10                  15

<210> SEQ ID NO 112
<211> LENGTH: 16
<212> TYPE: PRT
<213> ORGANISM: Homo Sapiens
<400> SEQUENCE: 112
Tyr Ile His His Ser Ala Gly Thr Tyr Tyr Asn Pro Ser Leu Lys Ser
 1               5                  10                  15
```

UNITED STATES PATENT AND TRADEMARK OFFICE
CERTIFICATE OF CORRECTION

| | |
|---|---|
| PATENT NO. | : 7,087,409 B2 |
| APPLICATION NO. | : 10/078757 |
| DATED | : August 8, 2006 |
| INVENTOR(S) | : Carlos F. Barbas, III et al. |

It is certified that error appears in the above-identified patent and that said Letters Patent is hereby corrected as shown below:

```
<210> SEQ ID NO 113
<211> LENGTH: 32
<212> TYPE: PRT
<213> ORGANISM: Mus Musculus
<400> SEQUENCE: 113
Arg Phe Thr Ile Ser Arg Asp Asn Ala Lys Asn Thr Leu Tyr Leu Gln
 1               5                  10                  15
Met Ser Ser Leu Asn Ser Glu Asp Thr Ala Met Tyr Tyr Cys Ala Arg
                20                  25                  30

<210> SEQ ID NO 114
<211> LENGTH: 32
<212> TYPE: PRT
<213> ORGANISM: Homo Sapiens
<400> SEQUENCE: 114
Lys Leu Thr Ile Thr Val Asp Glu Ser Thr Ala Thr Val Tyr Met Glu
 1               5                  10                  15
Met Arg Asn Leu Arg Ser Asp Asp Thr Ala Val Tyr Tyr Cys Ala Arg
                20                  25                  30

<210> SEQ ID NO 115
<211> LENGTH: 32
<212> TYPE: PRT
<213> ORGANISM: Homo Sapiens
<400> SEQUENCE: 115
Arg Val Thr Ile Ala Ile Asp Thr Ser Lys Asn Gln Leu Ser Leu Arg
 1               5                  10                  15
Leu Thr Ser Val Thr Ala Ala Asp Thr Ala Val Tyr Tyr Cys Ala Arg
                20                  25                  30
```

UNITED STATES PATENT AND TRADEMARK OFFICE
CERTIFICATE OF CORRECTION

PATENT NO.        : 7,087,409 B2
APPLICATION NO.   : 10/078757
DATED             : August 8, 2006
INVENTOR(S)       : Carlos F. Barbas, III et al.

It is certified that error appears in the above-identified patent and that said Letters Patent is hereby corrected as shown below:

```
<210> SEQ ID NO 116
<211> LENGTH: 32
<212> TYPE: PRT
<213> ORGANISM: Homo Sapiens
<400> SEQUENCE: 116
Arg Val Thr Ile Ser Val Asp Thr Ser Arg Asn Gln Ile Ser Leu Lys
1               5                   10                  15
Leu Arg Ser Val Thr Ala Ala Asp Thr Ala Val Tyr Tyr Cys Ala Arg
            20                  25                  30

<210> SEQ ID NO 117
<211> LENGTH: 32
<212> TYPE: PRT
<213> ORGANISM: Homo Sapiens
<400> SEQUENCE: 117
Arg Val Thr Met Ser Val Asp Thr Ser Lys Asn Gln Leu Ser Leu Lys
1               5                   10                  15
Leu Thr Ser Val Thr Ala Ala Asp Thr Ala Val Tyr Tyr Cys Ala Arg
            20                  25                  30

<210> SEQ ID NO 118
<211> LENGTH: 32
<212> TYPE: PRT
<213> ORGANISM: Homo Sapiens
<400> SEQUENCE: 118
Arg Val Thr Met Ser Ala Asp Thr Ser Lys Asn Gln Leu Ser Leu Lys
1               5                   10                  15
Leu Ala Ser Val Thr Ala Ala Asp Thr Ala Val Tyr Tyr Cys Ala Arg
            20                  25                  30

<210> SEQ ID NO 119
<211> LENGTH: 11
<212> TYPE: PRT
<213> ORGANISM: Mus Musculus
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<400> SEQUENCE: 119
Trp Gly Gln Gly Thr Leu Val Thr Val Ser Ala
1               5                   10

<210> SEQ ID NO 120
<211> LENGTH: 11
<212> TYPE: PRT
<213> ORGANISM: Homo Sapiens
<400> SEQUENCE: 120
Trp Gly Gln Gly Thr Leu Val Thr Val Ser Ser
1               5                   10

<210> SEQ ID NO 121
<211> LENGTH: 9
<212> TYPE: PRT
<213> ORGANISM: Artificial Sequence
<220> FEATURE:
<223> OTHER INFORMATION: LCDR3 variant portion
<221> NAME/KEY: VARIANT
<222> LOCATION: (3)...(6)
<223> OTHER INFORMATION: Xaa = any amino acid
<400> SEQUENCE: 121
Gln Gln Xaa Xaa Xaa Xaa Pro His Thr
1               5

<210> SEQ ID NO 122
<211> LENGTH: 8
<212> TYPE: PRT
<213> ORGANISM: Artificial Sequence
<220> FEATURE:
<223> OTHER INFORMATION: HCDR3 variant portion
```

UNITED STATES PATENT AND TRADEMARK OFFICE
CERTIFICATE OF CORRECTION

PATENT NO. : 7,087,409 B2
APPLICATION NO. : 10/078757
DATED : August 8, 2006
INVENTOR(S) : Carlos F. Barbas, III et al.

It is certified that error appears in the above-identified patent and that said Letters Patent is hereby corrected as shown below:

```
<221> NAME/KEY: VARIANT
<222> LOCATION: (1)...(4)
<223> OTHER INFORMATION: Xaa = any amino acid
<400> SEQUENCE: 122
Xaa Xaa Xaa Xaa Ser Phe Ala Tyr
 1               5
```

Signed and Sealed this

Sixteenth Day of January, 2007

JON W. DUDAS
*Director of the United States Patent and Trademark Office*